(12) United States Patent
Osterhout et al.

(10) Patent No.: US 8,765,122 B2
(45) Date of Patent: Jul. 1, 2014

(54) NANOSPHERE/MICROSPHERE DELIVERY SYSTEM FOR THE TREATMENT OF SPINAL CORD INJURY

(75) Inventors: Donna J. Osterhout, East Syracuse, NY (US); Julie M. Hasenwinkel, Manlius, NY (US); Dennis J. Stelzner, Syracuse, NY (US)

(73) Assignees: The Research Foundation of State University of New York, Albany, NY (US); Syracuse University, Syracuse, NY (US)

( * ) Notice: Subject to any disclaimer, the term of this patent is extended or adjusted under 35 U.S.C. 154(b) by 480 days.

(21) Appl. No.: 12/891,303

(22) Filed: Sep. 27, 2010

(65) Prior Publication Data

US 2011/0212136 A1 Sep. 1, 2011

Related U.S. Application Data

(63) Continuation-in-part of application No. 11/452,721, filed on Jun. 14, 2006, now abandoned, which is a continuation-in-part of application No. PCT/US2005/020730, filed on Jun. 14, 2005.

(60) Provisional application No. 60/579,568, filed on Jun. 14, 2004.

(51) Int. Cl.
*A61K 38/46* (2006.01)
(52) U.S. Cl.
USPC .... 424/94.6; 424/400; 424/130.1; 424/172.1; 424/85.2; 424/85.6; 424/85.7
(58) Field of Classification Search
None
See application file for complete search history.

(56) References Cited

U.S. PATENT DOCUMENTS

| 7,163,545 B2 | 1/2007 | Yaszemski et al. | |
|---|---|---|---|
| 2006/0078959 A1* | 4/2006 | Prabhakar et al. | 435/18 |

OTHER PUBLICATIONS

Hamann et al., Experimental Neurolgy, 2003, vol. 182, p. 300-309.*
NPL search results Jul. 11, 2013.*
Cao X. et al., "Delivering Neuroactive Molecules from Biodegradable Microspheres for Application in Central Nervous System Disorders", *Biomaterials* 20:329-339 (1999).
Kwon H-Y et al., "Preparation of PLGA Nanoparticles Containing Estrogen by Emulsification-Diffusion Method", *Colloids and Surfaces A: Physicochemical and Engineering Aspects* 182:123-130 (2001).
Bradbury E.J. et al., "Chondroitinase ABC Promotes Functional Recovery After Spinal Cord Injury", *Nature* 416:636-640 (2002).
Jain R.A., "The Manufacturing Techniques of Various Drug Loaded Biodegradable Poly(Lactide-co-Glycolide) (PLGA) Devices", *Biomaterials* 21:2475-2490 (2000).
Panyam J. et al., "Biodegradable Nanoparticles for Drug and Gene Delivery to Cells and Tissue", *Advanced Drug Delivery Reviews* 55:329-347 (2003).

* cited by examiner

*Primary Examiner* — Kade Ariani
(74) *Attorney, Agent, or Firm* — Scully, Scott, Murphy & Presser, P.C.

(57) ABSTRACT

A formulation including injectable biodegradable nanospheres and/or microspheres as a delivery system for chondroitinase ABC (cABC) or a functional derivative of cABC to treat acute and chronic spinal chord injury in a mammal having the same is provided. The biodegradable nanosphere/microsphere formulation releases cABC or a functional derivative of cABC in a time-released manner at the site of the spinal cord injury. cABC infusion can promote axon regrowth and some behavioral recovery. The nanospheres and/or microspheres provided herein include cABC or a functional derivative of cABC loaded within and/or on a biodegradable polymer matrix. In some embodiments of the present invention, the surface of the biodegradable polymer matrix can be modified to target a specific scar site. In addition to providing a nanosphere formulation that include polymeric incorporated cABC, a method of treating a mammal having a spinal cord injury is also provided.

19 Claims, 10 Drawing Sheets

NANOSPHERE/MICROSPHERE DELIVERY SYSTEM FOR THE TREATMENT OF SPINAL CORD INJURY

RELATED APPLICATIONS

This application is a continuation-in-part application of application Ser. No. 11/452,721 filed Jun. 14, 2006, which is a continuation-in-part application of PCT/US05/020730, filed Jun. 14, 2005, which claims benefit of U.S. Provisional Application No. 60/579,568, filed Jun. 14, 2004, the entire contents of each of which are incorporated herein by reference.

FIELD OF THE INVENTION

The present invention relates to biodegradable nanospheres and/or microspheres that release chondroitinase (cABC) and other therapeutic substances that promote healing, reduce scar formation and enhance nerve repair in a time-released manner at the site of a spinal cord injury (SCI). Moreover, the biodegradable nanospheres/microspheres of the present invention also promote axonal sprouting (i.e., local growth and new connections of regenerating and intact axons), and neuronal survival and sparing. The present invention also relates to a method for treating a mammal having a SCI with at least a nanosphere/microsphere formulation that includes biodegradable polymeric nanospheres or microspheres that are loaded with cABC. The nanosphere/microsphere formulation containing cABC can be administered at the site of the SCI.

BACKGROUND OF THE INVENTION

Traumatic spinal cord injury occurs in approximately 10-12,000 people per year in the United States. Most of the victims will survive the first year, and many will lead healthy and productive lives, although they will likely require a significant amount of care to maintain their well being. Given this, a person having a spinal cord injury is eager for treatment paradigms to promote repair and regain mobility. However, spinal cord injury presents an extremely complex set of problems to overcome to promote healing and reinnervation.

It was long thought that the central nervous system (CNS) lacked the ability to regenerate after injury. However, the use of peripheral nerve grafts in the brain and spinal cord that promoted axonal growth disproved this theory (Aguayo et al., "Axonal Elongation in Peripheral and Central Nervous System Transplants", Adv. Cell Neurobiol. 3:215-234, 1979; Benfey and Aguayo, "Extensive Elongation of Axons from Rat Brain into Peripheral Nerve Grafts", Nature 296:150-152, 1982). Peripheral neurons show a rapid response to injury, upregulating proteins associated with axon elongation, and are capable of regeneration. This is likely due to the presence of factors in the environment that stimulate process elongation and supply a permissive substrate to guide axon regrowth. In contrast, damage to the CNS initiates glial cell infiltration and pronounced scar formation, which ultimately inhibits repair and regeneration. However, Aguayo's results demonstrated that given the right substrate, CNS neurons retain the capacity to regenerate. Thus, failure of the adult neurons in the CNS to regenerate can be attributed to the local microenvironment.

Since this initial discovery, much work has been dedicated to identify conditions that will stimulate and guide axon regrowth in the CNS. At present, it is generally recognized that a multifaceted approach will be necessary to optimize repair and re-establish connections. First, for any reinnervation to occur, neurons have to survive the initial acute trauma. Successful treatment of chronic SCI would require this population of cells to survive for long periods. Second, the afflicted population of neurons has to be responsive to signals in the environment that stimulate axon regrowth. This may be problematic in adult neurons, where intracellular signaling mechanisms change with age, making the cells more responsive to inhibitory molecules (Cai et al., "Neuronal Cyclic AMP Controls the Developmental Loss in Ability of Axons to Regenerate", J. Neurosci. 21(13); 4731-4739, 2001). Third, there are a number of inhibitory molecules present in the lesion site that can actively block process elongation. Finally, the timing of any therapeutic treatment may also be important to optimize regrowth. It has been recently demonstrated that the acute immune response observed after injury is beneficial to the repair process. The infiltrating immune cells clear debris and secrete neuroprotective factors. Delayed administration of therapeutic treatments until after the peak immunological activity enhances neuronal survival and axonal regrowth (Coumans et al., "Axonal regeneration and functional recovery after complete spinal cord transection in rats by delayed treatment with transplants and neurotrophins", J. Neurosci 21:9334-9344, 2001). Thus, any successful treatment paradigm that is developed to treat SCI (either acute or chronic cases) will need to accommodate all of these factors.

Since the local microenvironment in the adult CNS is not conducive to spontaneous repair, one approach to stimulate repair is to change the environment to a more permissive one. This generally involves grafting a permissive substrate at the lesion site. The transplantation of Schwann cells (Xu et al., "A combination of BDNF and NT-3 promotes supraspinal axonal regeneration into Schwann cell grafts in the adult rat spinal cord", Exp. Neurol. 134:261-272, 1995), stem cells (Mc Donald et al., "Transplanted embryonic stem cells survive, differentiate and promote recovery in injured rat spinal cord", Nature Med. 5:1410-1412, 1999), or olfactory ensheathing cells (Li et al., "Regeneration of adult rat corticospinal axons induced by transplanted olfactory ensheathing cells", J Neurosci 18:10514-10524, 1998) have all been demonstrated to promote axonal elongation over the lesion site. The cells provide a positive substrate over which axons can grow, and likely secrete factors to promote survival and stimulate neurite outgrowth. Schwann cells, for example, are a rich source of extracellular matrix proteins and growth factors, and are the main reason that peripheral neurons can regenerate. However, in most studies, repair is limited; only a small percentage of axons have grown across the graft. There may be some behavioral improvement, but anatomically, it is difficult to show complete reinnervation of the targets. These findings suggest that other pharmacological approaches may be necessary to enhance recovery.

Another strategy involves promoting neuronal survival and axonal sprouting using neurotrophic and growth factors at the lesion site (Bregman et al., "Neurotrophic factors increase axonal growth after spinal cord injury and transplantation in the adult rat", Exp. Neurol. 148: 475-494, 1997; Kobayashi et al., "BDNF and NT-4/5 prevent atrophy of rat rubrospinal neurons after cervical axotomy, stimulate GAP-43 and Ta1-tubuln mRNA expression and promote axonal regeneration", J Neurosci. 17: 9583-9595, 1997; Liu et al., "Transplants of fibroblasts genetically modified to express BDNF promote regeneration of adult rubrospinal axons and recovery of forelimb recovery", J. Neurosci 19:4370-4387, 1999). However, these appear to work best when combined with graft implantation at the injury site and in fact, may be required to get elongation across the graft (Bregman et al., "Neurotrophic factors increase axonal growth after spinal cord injury and transplantation in the adult rat", Exp. Neurol. 148: 475-494, 1997). It is hypothesized that neurotrophins aid the damaged neurons in the host, and stimulate cells in the graft as well. They, in turn, secrete more molecules that can promote process outgrowth. Neuronal populations are responsive to a number of neurotrophins, depending on their expression of the Trk neurotrophin receptors (reviewed by Miller and Kaplan, "On Trk for retrograde signaling", Neuron 32(5): 767-70, 2001). Infusion of brain-derived neurotrophic factor (BDNF) and neurotrophin-3 (NT3) can increase sprouting and elongation through grey matter, but not much growth is observed through white matter. Again, recovery of function is limited in these studies, and the anatomical analysis has not demonstrated significant regrowth.

One consideration in treating adult CNS injury is that the neurons themselves may not be very responsive to the environmental cues that are present. Guidance molecules such as semaphorins, netrins and BDNF can be either attractive or repulsive depending on the intracellular cyclic AMP levels (Song et al., "cAMP-induced switching in turning direction of nerve growth cones", Nature 388: 275-279, 1997, Song et al., "Conversion of neuronal growth cones responses from repulsion to attraction by cyclic nucleotides", Science 281: 1515-1518, 1998). This is also true of myelin proteins such as myelin-associated glycoprotein (MAG), which has long been thought to inhibit neurite outgrowth. In fact, it is repulsive or attractive depending on the cyclic AMP concentration; if the cyclic AMP levels are high, MAG is a permissive substrate (Song et al., "Conversion of neuronal growth cones responses from repulsion to attraction by cyclic nucleotides", Science 281:1515-1518, 1998). The important finding is that adult neurons are less likely to elevate their cyclic AMP levels as compared with young neurons; thus, adult neurons are inhibited by MAG (Cai et al., "Neuronal cyclic AMP controls the developmental loss in ability of axons to regenerate", J Neurosci 21(13):4731-4739, 2001). Accordingly, changes in intracellular pathway may make it more difficult to stimulate axon outgrowth from adult neurons.

Another major reason for the failure of CNS neurons to regenerate is the abundance of molecules that inhibit neurite outgrowth. At present, there are two classes of inhibitory molecules that are largely responsible for this: myelin proteins, derived from damaged oligodendrocytes, and proteoglycans that comprise the glial scar.

Myelin contributes a number of proteins that have been shown to inhibit process outgrowth. The first to be identified was a protein called NogoA (reviewed by David and Lacroix, "Molecular approaches to spinal cord repair", Ann. Rev Neurosci. 26:411-40, 2003), which is found on the surface of oligodendrocytes and some axons. Others that can contribute to inhibition are myelin-associated glycoprotein (MAG), oligodendrocyte-myelin glycoprotein (OMgp), and the proteoglycan versican. These are all found in normal myelin, but when myelin is damaged, they are released at the injury site, and consequently restrict axon growth. Interestingly, they all signal through the receptor for Nogo, a protein called NgR. Thus, a reasonable strategy for enhancing repair is blocking the NgR receptor with an antibody, thus neutralizing the inhibitory molecules. Recent findings have shown that a blocking antibody to NogoA can enhance axonal sprouting and regrowth in the spinal cord after injury (Schnell and Schwab, "Axonal regeneration in the rat spinal cord produced by an antibody against myelin-associated neurite growth inhibitors", Nature 343:269-72, 1990 and Schnell and Schwab, "Sprouting and regeneration of lesioned corticospinal tract fibers in the adult rat spinal cord", Eur. J. Neurosci 5:1156-1172, 1993; Raineteau et al., "Spouting and regeneration after pyramidotomy and blockade of the myelin associated neurite growth inhibitors NI 35/250 in adult rats", Eur J. Neurosci 11:1486-1490, 1999).

The other source of major inhibitory activity lies with the formation of a glial scar after CNS injury (reviewed by Morgenstern et al., "Chondroitin sulfate proteoglycans in the CNS injury response" Prog. Brain Res. 137:313-332, 2002). The scarring process is rapid and complex, and involves a number of cell types. Astrocytes, meningeal cells, oligodendrocyte precursors and microglia can invade the injury site, and upregulate the synthesis and secretion of chondroitin sulfate proteoglycans (CSPG). CSPG accumulation occurs very rapidly at the lesion site, generally within one-week post injury. There are several types of CSPG expressed after injury, and include NG2, neurocan, versican, phosphocan and brevican. All of these molecules consist of a protein core with large glycosaminoglycan (GAG) sugar side chains attached. It is believed that the GAG side chains are responsible for the major inhibitory effects on axon elongation, by blocking access to growth promoting molecules. If the GAG chains are removed by chondroitinase ABC cleavage (cABC), axons can grow on a CSPG substrate. This has been demonstrated both in vitro and in vivo, with significant axon regrowth (Zuo et al., "Degradation of chondroitin sulfate proteoglycan enhances the neurite-promoting potential of spinal cord tissue", Exp. Neurol. 154:654-62, 1998; Moon et al, "regeneration of CNS axons back to their target following treatment of adult rat brain with chondroitinase ABC", Nat. Neurosci. 4:465-6, 2001; Bradbury et al., "Chondroitinase ABC promotes functional recovery after spinal cord injury", Nature 416:636-40, 2002). Thus, cABC administration is a promising treatment option for neutralizing inhibitors to axonal regeneration.

One limitation in the in vivo studies described above is the mode of application of the substances being tested as a treatment for SCI. Neurotrophins and cABC, for example, are often infused using repeated injections or mini-osmotic pumps. This mode of delivery may not be capable of delivering the optimal amounts of growth factor to the target site; for example, a large amount of neurotrophins pumped into a relatively wide area of the spinal cord may result in excessive sprouting, which, in turn, could lead to abnormal nerve connections. The duration and timing of treatments could also be problematic, especially if treatments are long term and need to change over time. A delivery system that is minimally invasive and that specifically targets the lesion site would be extremely useful in tailoring treatment therapies.

Loading molecules in biodegradable microspheres is one way to provide a sustained release in a localized target area. This has been applied with success to hormones (Johnson et el., "A month long effect from a single injection of microencapsulated human growth hormone", Nature Medicine 2(7) 795, 1996), vaccines (Alonso et al., "Biodegradable microspheres as controlled release tetanus toxoid delivery systems", Vaccine 12: 299-306, 1994) and chemotherapeutic agents (Rhines et al., "Local immunotherapy with interleukin-2 delivered from biodegradable polymer microspheres combined with interstitial chemotherapy: a novel treatment for experimental malignant glioma", Neurosurgery 52(4): 872-880, 2003). The composition can be varied to control the degradation time in vivo, and most conventional microspheres, such as polylactic/glycolic acid microspheres, have been show to be safe and effective in humans (Chaubal, "Polylactides/glycolides-excipients for injectible drug delivery and beyond", Drug Del Tech 2:34-36, 2002). The development of techniques to generate nanospheres (average diameter of less than 1 micron) makes them an even more attractive drug delivery system, as they are more easily injected at the desired treatment site.

In view of the above, there is a need for providing a means to treat acute and chronic spinal cord injury at the site of the spinal cord injury itself. Specifically, a formulation is required that can be administered at the site of the SCI which is capable of substantially reducing (i.e., effectively inhibiting) scar formation in acute and chronic cases.

SUMMARY OF THE INVENTION

The present invention provides a formulation that comprises injectable biodegradable carriers (e.g., nanospheres and/or microspheres) as a delivery system for chondroitinase ABC (cABC) or a functional derivative of cABC to treat acute and chronic spinal cord injury in a mammal having the same. Specifically, the present invention provides a biodegradable nanosphere/microsphere formulation that releases cABC or a functional derivative of cABC in a time-released manner at the site of the spinal cord injury. Previous studies have shown that cABC infusion can promote axon regrowth and some behavioral recovery.

The inventive nanospheres/microspheres containing cABC or a functional derivative of cABC are advantageous for the delivery of chondroitinase following spinal cord injury since they can be localized at the lesion. Surface charge modifications target the inventive nanospheres/microspheres to protein molecules at the injury site.

The inventive nanospheres/microspheres comprise cABC or a functional derivative of cABC loaded within and/or on a biodegradable polymer matrix. In some embodiments of the present invention, the outer surface of the biodegradable polymer matrix can be modified to target a specific scar site. Specifically, the outer surface of the polymer matrix can be modified to carry a positive or negative charge, depending on the charge characteristic of the specific inhibitory scar site. For example, positively charged nanospheres and/or microspheres containing cABC can be made which specifically target CSPG, a negatively charged molecule. The electrostatic attraction between the inventive nanospheres/microspheres and CSPG can target the loaded nanospheres/microspheres to the gliar scar and CSPG deposits.

In addition to providing a nanosphere/microsphere formulation that includes cABC-loaded polymeric nanospheres and/or microspheres, the present invention also provides a method of treating a mammal having a spinal cord injury by injecting the inventive nanosphere/microsphere formulation containing cABC-loaded nanospheres and/or microspheres to said mammal at the site of the spinal cord injury; and allowing said cABC to be released from said nanospheres and/or microspheres, wherein said released cABC substantially inhibits scar formation at said site of injury. Scar formation is effectively inhibited using the inventive method since the released cABC neutralizes the inhibitory elements that block axon regrowth. In addition to inhibiting scar formation, the treatment method of the present invention which includes the cABC-loaded polymeric nanospheres and/or microspheres can promote axonal sprouting (local axonal growth and new connections) and, in some instances, aide in neuronal survival and sparing.

In addition to the treatment method summarized above, the inventors of the present application also contemplate the incorporation of other therapeutic substances, which include, but are not limited to: antibodies, neurotrophins, growth factor hormones, proteins, etc. that promote neuronal survival and axon elongation through the glial scar and beyond the injury site. Therefore, cABC and other therapeutic substances can be administered together in a nanosphere/microsphere formulation, but released at various times to neutralize molecules that inhibit nerve growth and promote CNS regeneration. Alternatively, administration of a nanosphere/microsphere formulation containing the other therapeutic substances could occur independent of the administration of the cABC-containing formulation, i.e., at a time before administering the inventive cABC-loaded nanospheres and/or microspheres or at a time after administering the inventive cABC-loaded nanospheres and/or microspheres. Treatments that include both the cABC and other agents that promote neuronal survival and sparing as well as axon plasticity (i.e., sprouting) can be a means to customize treatment at the injury site and provide the signals needed at specific times to optimize axonal regrowth and repair after the spinal cord injury.

DETAILED DESCRIPTION OF THE INVENTION

Figure 1:
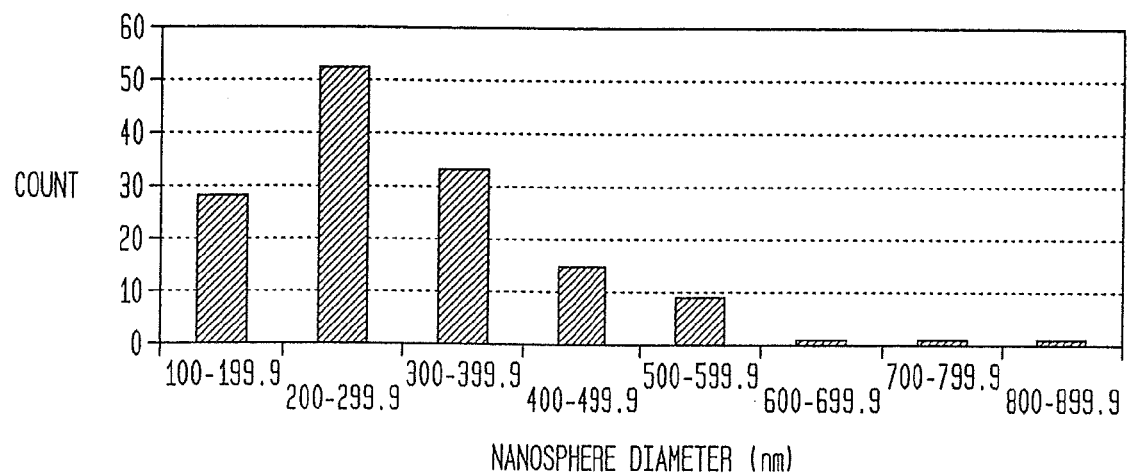
FIG. 1 shows nanosphere size distribution of a nanosphere formulation produced according to one embodiment of the present invention.

The present invention provides a nanosphere/microsphere formulation for the controlled release of cABC and other therapeutic substances that promote healing, reduce scar formation and enhance nerve repair in a mammal having a spinal cord injury. Moreover, it has been determined that the inventive nanosphere/microsphere formulation enhances axonal sprouting following a spinal contusion injury and, it can also be used to promote neuronal survival and sparing. The spinal cord injury can be an acute SCI or a chronic SCI. The nanospheres and/or microspheres of the present invention containing cABC release cABC at the site of the SCI in a controlled manner over a preselected time. The release of the aforementioned substances can be modulated by the composition and molecular weight of the polymer into which the cABC is loaded. The nanospheres and microspheres of the present invention are solid spherical particles, not hollow capsules. The cABC or other agents that could potentially be delivered by the present invention are incorporated or distributed throughout the bulk and at the surface of the nanospheres and/or microspheres during the fabrication process.

The failure of axonal regeneration is attributed to a number of inhibitory molecules that are present at the injury site. If the neuron survives the injury, the damaged axon must elongate and find its way back to the site of the target innervation. In the central nervous system, this is compromised by the expression of various molecules that inhibit axonal growth. These include myelin components and the formation of a glial scar soon after injury. The scar is composed of various molecules, including, an inhibitory proteoglycan called chondroitin sulfate (CSPG). Animal models of spinal cord injury have demonstrated that the sprouting may occur from the damaged axon, but is limited and generally ends at the gliar scar. Neutralization of such inhibitory molecules can enhance the regeneration.

The cABC released from the nanosphere/microsphere formulation of the present invention can efficiently neutralize CSPG, thereby inhibiting spinal cord scar formation and enhancing the nerve regeneration.

The cABC enzyme employed by the present invention may be either the natural cABC enzyme produced by and isolated from *Proteus vulgaris*, or a recombinant cABC enzyme produced by and isolated from other expression systems. Specifically, the DNA sequence that encodes the amino acid sequence of the cABC enzyme can be cloned from *Proteus vulgaris*, incorporated into one or more vectors (e.g., plasmids, phages, cosmids, phagemids, and viruses), and then recombinantly expressed in either a prokaryotic or eukaryotic host organism (e.g., *E. coli* bacteria or yeast). For example, Vikas Prabhakar and colleagues described a process for cloning the cABC-encoding DNA sequence from *Proteus vulgaris* and recombinantly expressing it in *E. coli* to form recombinant cABC I enzyme. See Prabhakar et al., "Chondroitinase ABC I from *Proteus vulgaris*: cloning, recombinant expression and active site identification," BIOCHEM. J., Vol. 386, pp. 103-112 (2005).

Further, the present invention may utilize a functional derivative of the cABC enzyme for neutralizing CSPG and treating SCI. As used herein, the term "functional derivative" of the cABC enzyme is a compound that possesses a biological activity (either functional or structural) that is substantially similar to that of the cABC enzyme. The term "functional derivative" is intended to include the biologically active fragments, variants, analogs and homologues, or the chemical derivatives of the cABC enzyme. The term "fragment" is meant to refer to any polypeptide subset of the cABC enzyme. The term "variant" is meant to refer to a molecule substantially similar in structure and function to either the entire cABC enzyme or to a fragment thereof The term "analog" refers to a molecule substantially similar in function to either the entire cABC enzyme or to a fragment thereof For example, the functional derivative of the cABC enzyme may preferably contain the middle domain of the cABC enzyme where the active site of the cABC enzyme is located, and more preferably the highly conserved residues His501, Tyr508, Arg560 and Glu653 that are critical and essential for the cABC enzymatic activity.

The term "nanospheres," "nanosphere," "microspheres," or "microsphere" is used throughout the present application to denote carrier structures that are biocompatible with and sufficiently resistant to chemical and/or physical destruction by the environment of use such that a sufficient amount of the nanospheres and/or microspheres remain substantially intact after injection into the site of the spinal cord injury. Typically, the carrier structures of the present invention range in size from about 1 nm to about 15 μm (15 microns). In different embodiments, the carrier structures have a size of about, at least, or no more than, for example, 1 nm, 2 nm, 5 nm, 10 nm, 20 nm, 30 nm, 40 nm, 50 nm, 60 nm, 70 nm, 80 nm, 90 nm, 100 nm, 150 nm, 200 nm, 250 nm, 300 nm, 350 nm, 400 nm, 450 nm, 500 nm, 550 nm, 600 nm, 650 nm, 700 nm, 750 nm, 800 nm, 850 nm, 900 nm, 950 nm, 1 μm (1000 nm), 1.1 μm, 1.2 μm, 1.3 μm, 1.4 μm, 1.5 μm, 1.6 μm, 1.7 μm, 1.8 μm, 1.9 μm, 2 μm, 2.1 μm, 2.2 μm, 2.3 μm, 2.4 μm, 2.5 μm, 2.6 μm, 2.7 μm, 2.8 μm, 2.9 μm, 3 μm, 3.1 μm, 3.2 μm, 3.3 μm, 3.4 μm, 3.5 μm, 3.6 μm, 3.7 μm, 3.8 μm, 3.9 μm, 4 μm, 4.1 μm, 4.2 μm, 4.3 μm, 4.4 μm, 4.5 μm, 4.6 μm, 4.7 μm, 4.8 μm, 4.9 μm, 5 μm, 6 μm, 7 μm, 8 μm, 9 μm, 10 μm, 11 μm, 12 μm, 13 μm, 14 μm, or 15 μm, or a range bounded by any two of the foregoing exemplary sizes. In particular embodiments, the carrier structures have a size within a range of 700 nm-15 μm, 750 nm-15 μm, 800 nm-15 μm, 850 nm-15 μm, 900 nm-15 μm, 1-15 μm, 2-15 μm, 3-15 μm, 4-15 μm, 5-15 μm, 700 nm-10 μm, 750 nm-10 μm, 800 nm-10 μm, 850 nm-10 μm, 900 nm-10 μm, 1-10 μm, 2-10 μm, 3-10 μm, 4-10 μm, 5-10 μm, 700 nm-5 μm, 750 nm-5 μm, 800 nm-5 μm, 850 nm-5 μm, 900 nm-5 μm, 1-5 μm, 2-5 μm, 3-5 μm, 4-5 μm, 700 nm-1 μm, 750 nm-1 μm, 800 nm-1 μm, 850 nm-1 μm, or 900 nm-1 μm. A carrier size of at least 700 nm, 750 nm, or 1 μm, and up to or less than 15 μm, 10 μm, or 5 μm, is particularly advantageous in that a carrier within any of these size ranges is small enough to be injectable while large enough to substantially not enter cells.

The cABC and other therapeutic substances that promote healing, reduce scar formation and enhance nerve repair in a mammal having a spinal cord injury are loaded within and/or on the nanospheres/microspheres. In some embodiments, the carrier structures contain a hollow portion wherein chondroitinase is contained, while in other embodiments, the carrier structures are solid (i.e., do not contain a hollow portion) so that chondroitinase is contained admixed with polymeric material throughout the carrier.

The polymeric material that can be employed in the present invention for forming the nanospheres and/or microspheres includes any biocompatible and biodegradable homopolymer or copolymer. The term "biocompatible" denotes that the polymeric material is compatible with a living tissue or a living organism by not being toxic or injurious and by not causing immunological reaction. The term "biodegradable" denotes that the polymeric material will degrade over time by action of enzymes, by hydrolytic action and/or by similar mechanisms in the body of a subject.

Suitable examples of polymeric materials that can be employed in the present invention include, but are not limited to: aliphatic polyesters, e.g., homopolymers or copolymers synthesized from one or more kinds of α-hydroxycarboxylic acids (e.g., glycolic acid, lactic acid, 2-hydroxybutyric acid, and valinic acid, leucic acid), hydroxydicarboxylic acids (e.g., malic acid), hydroxytricarboxylic acids (e.g., citric acid), or their mixtures; poly-α-cyanoacrylic esters, e.g., poly (methyl α-cyanoacrylate), poly(ethyl α-cyanoacrylate), poly (butyl α-cyanoacrylate); and amino acid polymers, e.g., poly (γ-benzyl-L-glutamate), or their mixtures. The mode of polymerization for these biodegradable polymers may be any of random, block or graft polymerization technique.

Preferred biodegradable polymers employed in the present invention are aliphatic polyesters, e.g., homopolymers or copolymers synthesized from one or more kinds of α-hydroxycarboxylic acids (e.g., glycolic acid, lactic acid, and 2-hydroxybutyric acid). Particularly preferred aliphatic polyesters are copolymers synthesized from two or more kinds of α-hydroxycarboxylic acids. These copolymers can also be used as mixtures.

When the α-hydroxycarboxylic acids are chiral compounds, they may be any of D-, L- and D-, L-configuration. It is preferable that the ratio of the D-/L-configuration (mol %) is in the range from about 75/25 to about 25/75. More preferred is a α-hydroxycarboxylic acid wherein the ratio of the D-/L-configuration (mol %) is in the range from about 60/40 to about 30/70.

An example of the above mentioned α-hydroxycarboxylic acid polymer is a lactic acid polymer (hereinafter sometimes referred to as "polylactic acid"). The α-hydroxycarboxylic acid copolymer includes copolymers of glycolic acid with the other α-hydroxycarboxylic acids such as lactic acid and 2-hydroxybutyric acid. A preferred α-hydroxycarboxylic acid copolymer is lactic acid-glycolic acid copolymer.

The polylactic acid may be either D-configuration or L-configuration or a mixture; one with the D-/L-configuration ratio (mol %) of about 75/25 to about 20/80 is preferred. More preferred is a polylactic acid wherein the ratio of the D-/L-configuration (mol %) is in the range of about 60/40 to about 25/75.

The polylactic acid preferably has a weight average molecular weight of about 20,000 to about 150,000. More preferred is a polylactic acid having a weight average molecular weight of about 50,000 to about 120,000. The polylactic acid can be produced by art recognized methods including, for example, the dehydrative polycondensation in the absence of a catalyst or by dehydrative polycondensation in the presence of an inorganic solid acid catalyst.

The compositional ratio (lactic acid/glycolic acid, mol %) in the polymeric lactic acid-glycolic acid (PLGA) copolymer is about 100/0 (homopolymer) to about 40/60, preferably about 90/10 to about 45/55, and more preferably about 85/15 to 50/50. The weight average molecular weight of the PLGA copolymer is preferably about 20,000 to about 150,000, and more preferably about 50,000 to about 120,000.

The glycolic acid copolymers (e.g., lactic acid-glycolic acid copolymer, 2-hydroxybutyric acid-glycolic acid copolymer, etc.) may be used alone or in an admixture with polylactic acid. When glycolic acid copolymer is used in combination with polylactic acid, the ratio of glycolic acid copolymer/polylactic acid (weight %) can be, for example, about 10/90 to about 90/10. The preferred ratio is about 20/80 to about 80/20. The present invention also contemplates pure PGA nanospheres and microspheres, without added PLA.

In addition to the above mentioned biodegradable polymers, the present application also includes the use of poly (ethylene glycol)/poly(latic-co-glycolic acid) PLGA copolymers and poly(caprolactone) PCL (another aliphatic polyester polymer that is much slower in degrading as compared with PLA or PLGA, i.e., poly(latic-co-glycolic acid)). Poly(ethylene glycol) or PEG is synonymous with poly(ethylene oxide) or PEO. In other embodiment of the present invention, nanosphere/microsphere formulations including PEG-PLGA are contemplated. When these particles are placed in an aqueous environment, the PEG block of the polymeric material is much more hydrophilic and it orients itself to the outer shell of the particle; the PLGA block remains in the core. As is known to one skilled in the art, PEG inhibits protein binding and cellular recognition, making the particles 'stealthy' and reducing cellular uptake and phagocytosis. In yet another embodiment of the present invention, PEG can be blended with a stabilizer such as, for example, poly(vinyl alcohol) and/or didodecyl dimethyl ammonium bromide (DMAB) which physically absorbs the polymer to the surface of the nanosphere/microsphere.

The degradation process of the above-mentioned polymers, either in vivo or in vitro, is affected by several factors, including preparation method, molecular weight, composition, chemical structure, size, shape, crystallinity, surface morphology, hydrophobicity, glass transition temperature, site of active component implantation, physicochemical parameters in the surrounding environment (such as pH, temperature and ionic strength), and mechanism of hydrolysis. Specifically, the degradation behavior of nanospheres and/or microspheres depends on hydrophilicity of the polymer: the more hydrophilic the polymer, the more rapid its degradation. The hydrophilicity of the polymer is influenced by the ratio of crystalline to amorphous regions, which in turn is determined by copolymer composition and monomer stereochemistry. For example, PLGA copolymer prepared from L-PLA and PGA are crystalline copolymers, while those from D, L-PLA and PGA are amorphous in nature. Lactic acid, being more hydrophobic than glycolic acid, makes lactic acid-rich PLGA copolymers less hydrophilic and subsequently slows down the degradation process.

In general, the degradation time will be shorter for low molecular weight, more hydrophilic, more amorphous polymers and copolymers with higher content of glycolic acid. In accordance with these variables, the in vivo degradation rate of the D, L-PLGA copolymer may vary from a few weeks to more than 1 year.

The in vivo biodegradation of the polymeric nanospheres and/or microspheres is important because it determines the rate and mechanism of release of the therapeutic agent carried by such nanospheres and/or microspheres. The release of therapeutic agent from the polymeric matrix of the nanospheres and/or microspheres is biphasic, i.e., including an initial phase of diffusion through the polymeric matrix and a subsequent phase of both diffusion of the therapeutic agent through the polymeric matrix and the degradation of the polymeric matrix itself.

Therefore, by controlling the in vivo degradation rate of the polymeric nanospheres and/or microspheres that carry the cABC enzyme, the release rate of the cABC enzyme can be readily adjusted. Preferably, the nanosphere/microsphere formulation of the present invention contains cABC-loaded nanospheres and/or microspheres that release cABC for an extended period, e.g., ranging from about 1 week to about 1 year. More preferably, the nanosphere/microsphere formulation of the present invention contains cABC-loaded nanospheres and/or microspheres that release cABC at different rates, so that the overall release pattern of the cABC can be readily adapted for specific applications.

There are several common methods for the preparation of biodegradable nanospheres and/or microspheres made from polymers and co-polymers that can be used in the present invention in fabricating the inventive nanospheres/microspheres containing cABC. For example, solvent-evaporation, salting-out, nanoprecipitation, and emulsification-diffusion can be used. Each of the foregoing methods is well known in the art. For example, the general procedures disclosed in Gurny et al., "Development of biodegradable and injectable latices for controlled release of potent drugs", Drug Dev. Ind.

Pharm., 7:1-25, 1981, Bindschaedler et al., "Process of preparing a powder of water-insoluble polymer which can be redispersed in a liquid phase, the resulting powder and utilization thereof", U.S. Pat. No. 4,468,350, 1990, Allèmann, et al., "Preparation of aqueous polymeric nanodispersions by a reversible salting-out process: influence of process parameters on particle size", Int. J. Pharm., 87:247-253 1992; Fessi et al., "Procédé de préparation de systèmes colloïdaux dispersibles d'une substance, sous forme de nanoparticules", French Patent, 2,608,988, 1998, Leroux, "New approach for the preparation of nanoparticles by an emulsification-diffusion method", Eur. J. Pharm. Biopharm., 41:14-18, 1995, Gaspar et al., "Formulation of L-asparaginase-loaded poly (lactide-co-glycolide) nanoparticles: influence of polymer properties on enzyme loading, activity and in vitro release", J. Control. Rel. 52:53-62, 1998; Wolf et al., "Stabilisation and determination of the biological activity of L-asparaginase in poly(D,L-lactide-co-glycolide) nanospheres", Int. J. Pharm. 256:141-152, 2003, Kwon et al., "Preparation of PLGA nanoparticles containing estrogen by emulsification-diffusion method", Coll. and Surf. A: Physicochem. and Eng. Asp. 182:123-130, 2001, Blanco and Alonso, "Development and characterization of protein-loaded poly(lactic/glycolic acid) nanospheres", Eur. J. Pharm. Biopharm. 43:285-294, 1997, Vila et al., "Design of biodegradable particles for protein delivery", J. Control. Rel. 78 15-24, 2002, Sahoo et al., "Residual polyvinyl alcohol associated with poly(D,L-lactide-co-glycolide) nanoparticles affects their physical properties and cellular uptake", J. Control. Rel. 82:105-114, 2002, Song et al., "cAMP-induced switching in turning direction of nerve growth cones", Nature 388: 275-279, 1997, Avgoustakis et al., "PLGA-mPEG nanoparticles of cisplatin: in vitro nanoparticle degradation, in vitro drug release and in vivo drug residence in blood properties", J. Control. Rel. 79:123-135, 2002, and Labhasetwar et al., "Arterial uptake of biodegradable nanoparticles: effect of surface modifications", J. Pharm. Sci. 87:1229-1234, (1998) can all be employed in fabricating the inventive nanospheres/microspheres containing cABC. The techniques disclosed in the aforementioned references for making the polymeric nanosphere/microsphere matrix are incorporated herein by reference.

Of the various techniques, it is preferred to use a solvent-evaporation technique or an emulsification-diffusion technique in fabricating the inventive nanospheres and/or microspheres that release active cABC. The emulsification-diffusion technique may offer some advantages over the solvent-evaporation technique including, for example, an easier fabrication process, the potential for smaller nanospheres and/or microspheres, and the ability to readily modify the surface of the polymeric matrix by using a stabilizer rather than having an additional surface modification step, as would be required in solvent evaporation.

Preferably, the outer surface of the cABC-loaded polymeric nanospheres and/or microspheres can be modified to carry a positive or negative charge, which enhances adhesion of the nanospheres and/or microspheres to an oppositely charged inhibitory molecular or scar site. For example, positively charged nanospheres and/or microspheres containing cABC demonstrate significantly better adhesion to the negatively charged CSPG molecule at the glial scar site, in comparison with un-charged nanospheres and/or microspheres. Therefore, the surface-modified nanospheres and/or microspheres can be used in the present invention to localize cABC enzyme to the scar site for more effective treatment of the SCI, which is an important feature of the present invention. Further, surface charge can reduce aggregation of nanospheres and therefore enhance stability of the nanosphere formulation of the present invention.

Further details concerning the preferred methods of fabricating the inventive nanospheres and/or microspheres using a solvent-evaporation and an emulsification-diffusion method are now provided:

I. Solvent-Evaporation Method

In one embodiment, the inventive nanospheres and/or microspheres can be prepared by a water-in-oil-in-water (w/o/w) solvent evaporation technique, such as described, for example, by Blanco et al., "Development and characterization of protein-loaded poly(lactic/glycolic acid) nanospheres", Eur. J. Pharm. Biopharm. 43:285-294, (1997). In such a technique, one of the above mentioned polymeric materials, such as, for example, PLGA can be dissolved in an organic solvent, such as, ethyl acetate, to a concentration from about 2 to about 10 (w/v) and emulsified with an aqueous solution of reconsitituted cABC by probe sonication. The reconsitituted cABC (0.1 to 100 U/ml), which may optionally, but not necessarily, include BSA (Bovine Serum Albumin) or other carrier molecules as described in greater detail hereinafter, can be added in an amount from about 0.01 to about 1.0%, or in any other amount that would result in nanospheres/microspheres that release cABC in concentrations sufficient to effectively reduce CSPG in the glial scar with little or no toxic effects and undesired inflammatory response, which can be readily determined by a person ordinarily skilled in the art through routine experimentation. These steps produce a water/oil emulsion (w/o), which can be further emulsified by sonication in an aqueous solution of an emulsifier such as PVA (1%, w/v) to form a second water/oil/water emulsion (w/o/w). The double emulsion can then be diluted into an aqueous solution of PVA and stirred for a time to evaporate the organic solvent. The nanospheres and/or microspheres so formed can then be collected by known means including, for example, centrifugation, washed with distilled, deionized water, and then lyophilized using methods known to those skilled in the art.

Surface modification of the resultant nanospheres and/or microspheres loaded with cABC can be made by treating the nanospheres/microspheres with either a cationic surfactant or an anionic surfactant. The type of surfactant employed depends on the charge of the site being treated. The surfactants used in modifying the nanospheres/microspheres of the present invention can be any pharmaceutical acceptable cationic or anionic surfactant. Cationic surfactants are used in forming positively charged nanospheres/microspheres which, in turn, are attracted by negatively charged sites. Examples of cationic surfactants that can be employed in the present invention include, but are not limited to: didodecyl dimethyl ammonium bromide and chitosan. Anionic surfactants are used in forming negatively charged nanospheres/microspheres which, in turn, are attracted by positively charged sites. Examples of anionic surfactants that can be employed in the present invention include, but are not limited to: polyvinyl alcohol.

The amount of surfactant used to modify the nanosphere/microsphere surface may vary depending on the amount of nanospheres and/or microspheres being treated. The surfactants can be admixed with water to provide an aqueous solution. In such an embodiment, the aqueous solution contains from about 1 to about 10% surfactant.

The surface modification occurs by contacting the nanospheres and/or microspheres with the surfactant and providing a suspension by sonication over an ice bath. The suspension is then frozen over dry ice and lyophilized.

II. Emulsification-Diffusion Method Nanospheres and/or microspheres of the present invention can also be prepared using the procedure disclosed, for example, in Quintanar-Guerrero et al., "Influence of stabilizing agents and preparative variables on the formation of poly (D,L-lactic acid) nanoparticles by an emulsification-diffusion technique", Int. J. Pharm. 143:133-141, (1996) and Kwon et al., "Preparation of PLGA nanoparticles containing estrogen by emulsification-diffusion method", Coll. and Surf. A: Physicochem. and Eng. Asp. 182:123-130, (2001). In such a method, one of the above mentioned polymeric materials, such as PLGA, is dissolved in an organic solvent to a concentration from about 1 to about 5% w/v, followed by the addition of reconstituted cABC, which may optionally, but not necessarily, include BSA or other carrier molecules. The amount of reconstituted cABC can be within the ranges mentioned above, or in any other range that would result in nanospheres/microspheres that release cABC in concentrations sufficient to effectively reduce CSPG in the glial scar with little or no toxic effects and undesired inflammatory response, which can be readily determined by a person ordinarily skilled in the art through routine experimentation. This organic phase mixture is then emulsified with an aqueous solution of an emulsifier such as PVA after mutual saturation of the two phases, using a high-speed homogenizer (8000 rpm).

In order to obtain surface modified nanospheres and/or microspheres using the emulsification-diffusion technique, the organic phase will be emulsified with a cationic or anionic surfactant rather than PVA, under the conditions previously described. Following this step, water is added to the emulsion under magnetic stirring in order to allow for diffusion of organic solvent into the water and subsequent nanoprecipitation of the polymer. The organic solvent is then removed by filtration and the nanospheres and/or microspheres are then lyophilized.

The methods described above can be readily used for preparation of nanospheres and/or microspheres with sizes varying from a few nanometers to several hundred micrometers, by controlling the stirring rate and other processing conditions.

Preferably, the formulation of the present invention contains nanospheres having diameters ranging from about 100 nm to about 900 nm, and more preferably from about 250 nm to about 750 nm, which can be easily injected in vivo, but which are large enough to remain extra-cellular and therefore induce a minimal inflammatory response when injected. FIG. 1 shows an exemplary size profile for a cABC-loaded nanosphere formulation, which was produced according to one embodiment of the present invention.

Notwithstanding the technique used in forming the inventive nanospheres/microspheres, the loading of the same with various concentrations of cABC can be achieved by using a stock solution of about 5 units/ml of cABC. The loading efficiency can be determined by two different methods. First, the washings from the preparation techniques are collected and analyzed for residual cABC content using SDS gel electrophoresis. The amount of loaded enzyme cABC is determined by the difference in the total amount of cABC added and the amount that is not incorporated, as measured by this technique. The loading efficiency is the ratio of enzyme incorporated to the total amount of cABC used in the fabrication process, expressed as a percentage.

The other method for evaluating enzyme loading efficiency is a direct assay of cABC content following an accelerated hydrolysis of the polymeric nanospheres and/or microspheres. Samples of enzyme-loaded nanospheres and/or microspheres are added to a 0.1 M sodium hydroxide solutions (NaOH) containing 2% w/v sulfate dodecyl sodium (SDS) and shaken overnight. The solutions are neutralized with 1 M hydrochloric acid (HCl), diluted with distilled water, and filtered through a 0.2 μm Millipore membrane. The solutions are then analyzed by SDS gel electrophoresis and the enzyme loading efficiency will be determined as a function of fabrication technique and surface modification.

In addition to fabricating nanospheres/microspheres that are loaded with cABC, other therapeutic substances that that promote healing, reduce scar formation and enhance nerve repair of a spinal cord injury (SCI) can be loaded to nanosphere/microsphere matrix using the techniques described above. The loading of the other substances is within the ranges mentioned above, and the above-mentioned techniques can be used in loading these other therapeutic substances onto the nanosphere/microsphere matrix, which that can be administered either in conjunction with or independent of cABC.

A unique feature of the nanosphere/microsphere delivery system of the present invention is the ability to incorporate other therapeutic substances in the nanospheres and/or microspheres, in addition to cABC, which can be injected together but released at various times, to neutralize molecules which inhibit nerve growth and promote CNS regeneration.

The other substances that can be loaded within the nanospheres/microspheres include, but are not limited to: enzymes, proteins, and antibodies. For example, neurotrophic molecules, such as Nerve Growth Factor (NGF), Brain-Derived Neurotrophic Factor (BDNF), Neurotrophin (NT) 3, 4/5, and 6, Ciliary Neurotrophic Factor (CNTF), Glial Cell Line-Derived Growth Factor (GDNF), Leukemia Inhibitory Factor (LIF), Interleukin 6 (IL6), Interleukin 11 (IL 11), and Cardiotrophin 1, and growth factor hormones, such as Interferon α (IFNα), Interferon β (IFNβ) and Tumor Necrosis Factor (TNF), can be incorporated into the nanospheres/microspheres of the present invention. Further, proteoglycans, such as decorin, or antibodies that block the inhibitory activity of certain proteoglycans (such as NG2 proteoglycan) can further be incorporated into the nanospheres/microspheres of the present invention. Carrier proteins, such as Bovine Serum Albumin (BSA), Keyhole Limpet Hemocyanin (KLH), Ovalbumin (OVA), Fetal Bovine Serum (FBS), Thyroglobulin (THY), and Human Serum Albumin (HSA), can optionally be loaded within the nanospheres/microspheres by using the above described methods. Such carrier proteins can enhance the stability of cABC enzyme in vivo. Therefore, use of such carrier proteins is an optional, but not necessary, feature of the present invention. Further, monoclonal or polyclonal antibodies that target inhibitory substances present in the scar, such as myelin or myelin proteins, or target the receptors for these molecules, can be incorporated into the nanospheres/microspheres of the present invention.

The nanospheres and/or microspheres of the present invention can also additionally include pharmaceutically acceptable carriers and/or excipients—loaded within the polymeric matrix. As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for injection into the spinal cord. Excipients include, for example, pharmaceutically acceptable stabilizers and disintegrants.

The nanospheres and/or microspheres containing cABC can be administered alone in one possible treatment program. Alternatively, a treatment program can be devised in which nanospheres containing cABC and nanospheres containing other therapeutic substances that promote healing, reduce scar formation and enhance nerve repair can be conjointly used.

The nanospheres and/or microspheres of the present invention are administered to a mammal having a spinal cord injury at the site of the injury itself by first suspending the nanospheres and/or microspheres in an aqueous vehicle and then injected through a hypodermic needle with a micropipette tip. Prior to injection, the nanospheres and/or microspheres can be sterilized with, preferably, gamma radiation or electron beam sterilization using techniques well known to those skilled in the art.

The inventive nanospheres and/or microspheres can be injected anytime after the spinal cord injury and the dosage may vary depending on the severity of the spinal cord injury. Typically, the dosage of nanospheres and/or microspheres injected into a subject is from about 0.5 µL to about 100 µL of chondroitinase, with a dosage from about 3 µL to about 20 µL being more typical. The above ranges are within therapeutic ranges which are capable of promoting healing, reducing scar formation and enhancing nerve repair at the site of the spinal cord injury. In different embodiments, the dosage of chondroitinase is 0.5, 1, 1.5, 2, 2.5, 3, 3.5, 4, 4.5, or 5 µL, or within a range bounded by any two of the foregoing exemplary dosages.

The nanospheres and/or microspheres of the present invention are designed to degrade over time in an aqueous environment, resulting in the release of cABC, and other the substances that promote healing, reduce scar formation and enhance nerve repair at the site of a spinal cord injury. The time of release may vary depending on the type of polymeric materials used in forming the inventive nanospheres and/or microspheres, as described hereinabove. A slow release formulation or an immediate formulation can be made by varying the polymeric composition and molecular weight. Typically, the release of the cABC and other substances from the nanospheres of the present invention is from about 24 hours to about 120 days. More preferably, the release of the cABC and other substance from the nanospheres of the present invention is from about 48 hours to about 30 days.

Figure 2:
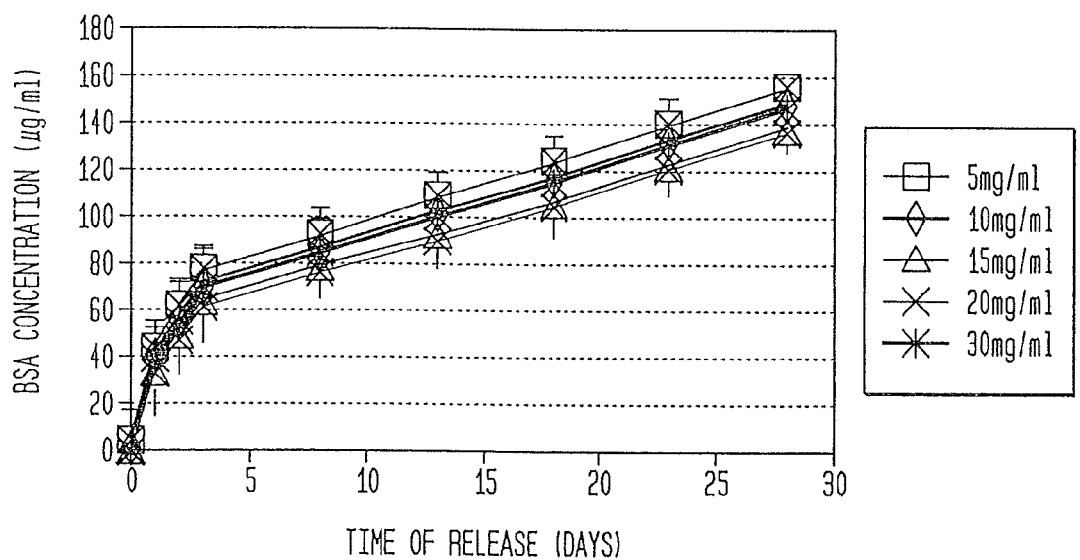
FIG. 2 shows time-release results of cationic nanospheres that are loaded with Bovine Serum Albumin (BSA) at different concentrations over a 30-day period.

The time-release property of the nanosphere/microsphere formulation of the present invention can be readily measured in vitro by Bradford protein assays. For example, FIG. 2 shows the release of Bovine Serum Albumin (BSA) by BSA-loaded cationic nanospheres over a 30-day period. Sustained BSA release for at least 4 weeks was observed, following an initial burst in 1-2 days. The BSA-loaded cationic nanospheres were provided at different concentrations, e.g., ranging from about 5 mg/ml to about 30 mg/ml, but the release curves are substantially the same, indicating that release of BSA by the nanospheres is not affected by the concentration of the nanospheres.

The following examples are provided to illustrate the fabrication of the inventive nanospheres and/or microspheres together with some advantages that can be obtained therefrom.

Example 1

I. Preparation Loaded PLGA Microspheres

In this example, microspheres were prepared through a water-in-oil-in-water (WOW) emulsion and solvent evaporation/extraction technique described by Xu et al., "Polyphosphoester microspheres for sustained release of biologically active nerve growth factor", Biomaterials 23:3765-3772, 2002. This method utilizes three phases: (1) an inner water phase enclosing the protein, (2) an intermediary organic phase consisting of a polymer/methylene chloride solution, and (3) an outer water phase containing an emulsifying agent. First, 85/15 PLGA was dissolved in methylene chloride at a concentration of 5% (w/v). BSA solution (90 ul of 30%; Sigma) and 900 µl of polymer solution were emulsified by probe sonication (IKA—WERKE, Staufen, Germany) at an output of 3 for 20 s. This emulsion was poured into an aqueous solution of polyvinyl alcohol (PVA; 10%) and vortexed for 3 min. The solution was then added to 20 ml of 0.3% PVA solution with 5% NaCl, and stirred with a magnetic stirrer for 3 h to evaporate the organic solvent. The microspheres were collected by centrifugation and washed three times with distilled, deionized water. Microspheres were stored in a dessicator until use.

In addition to the BSA encapsulated microspheres, microspheres with bromodeoxyuridine (BRDU) or chondroitinase ABC were also prepared by similar methods. Specifically, two separate preparations were manufactured by the same method outlined above, with either 30 microliters of BRDU (100 ug/ml) or 90 microliters of BRDU (25 ug/ml) added to the BSA emulsion. The same technique was employed to generate chondroitinase ABC (cABC) incorporated microspheres, using 30 microliters of reconstituted cABC (Sigma; 5 units per ml) added to the emulsion.

Scanning Electron Microscopy

The morphology and size of microspheres was evaluated through scanning electron microscopy (JSM-5600, JOEL, Peabody, Mass.). BSA-loaded microspheres (stored dry in a dessicator) were mounted on double-adhesive tape then sputter coated with gold prior to imaging.

Results:

Microspheres, loaded with BSA, BRDU, or chondroitinase ABC were fabricated using the above described procedure. The SEM data showed that they were rather uniform in shape and size. The average diameter was 156 microns, measured in several independent preparations.

Measurement of Protein Release

BSA-loaded microspheres were immersed in 1 ml of PBS at two concentrations, 15 mg/ml and 30 mg/ml. At each time point, 160 µl aliquots were taken in triplicate, BSA content was measured using a Bradford protein assay (BioRad), and read by microplate reader at 600 nm. The remaining supernatant was decanted and replaced with fresh PBS each time the supernatant was sampled. Cumulative release profiles, along with total protein release were plotted over time.

Results:

The release of BSA was immediate, as it was detected 24 hours post immersion. The BSA release continued for at least 2½ weeks. Physically, the microspheres themselves did not completely degrade, but settled in the bottom of the tube and remained there for the duration of the experiment. They were still visible in the test tube one month post immersion. The data demonstrates that this particular PLGA formulation degrades slowly.

BSA-loaded nanospheres having diameters in the range of from about 250 nm to about 750 nm were also manufactured, by adjusting the stirring rate and other process conditions. Nanospheres of such sizes are easy for injected, and they remain extra-cellular both in vitro and in vivo. The results from the initial release study of the nanospheres were very similar to that observed with the microspheres. BSA was detected 24 hours post immersion, and was still detectable by Bradford assay one week later. The cumulative amount of BSA was less than observed with the microspheres, but that was to be expected since the beads were at least 10 fold less in size than the microspheres.

Bioassays

The next set of experiments assessed the ability of the nanospheres and/or microspheres to deliver a substance to live cells, without evidence of cellular toxicity. To evaluate the effects in a biological system, two different preparations of nanospheres and/or microspheres were tested.

First, microspheres were loaded with bromodeoxyuridine (BRDU), a uridine analog that can label dividing cells. If BRDU is present in the culture media, proliferating cells will incorporate it into newly synthesized DNA. Therefore, BRDU is typically used as a marker for dividing cells. In these experiments, aliquots of microspheres were incubated in culture with proliferating PC12 cells. The beads were left in culture for various times, including 8 hrs, 12 hrs, 24 hrs, 36 hrs and 48 hrs. At the appropriate time point, the cells were fixed in 4% paraformaldehyde and stained for BRDU incorporation using standard immunocytochemical techniques.

Figure 3:
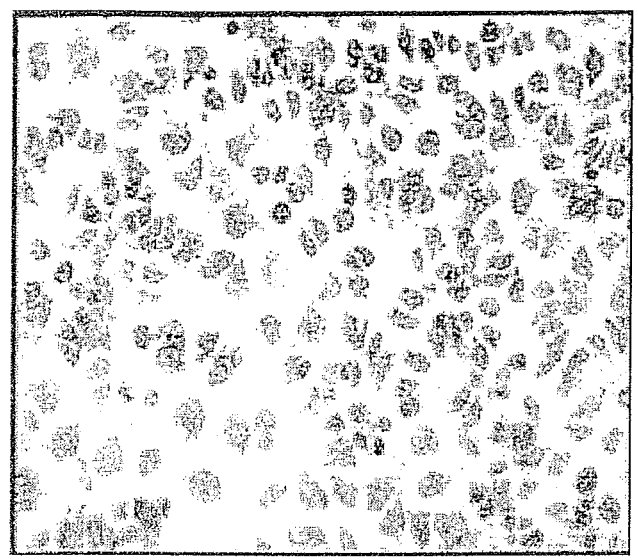
FIG. 3 shows incorporation of bromodeoxyuridine (BRDU) into PC12 cells, while BRDU was carried by the microspheres of the present invention.

Results:

BRDU release was quick, BRDU incorporation was visualized after only an 8-hour incubation time, as shown in FIG. 3. More surprisingly, cellular toxicity was not observed with the microspheres in culture. The cells remained attached, proliferated, and no cell death was observed in any of the cultures, even if the microspheres were in contact with the cells.

The second bioassay was a neurite outgrowth assay, designed to test the release of cABC from nanospheres and/or microspheres in vitro. Primary embryonic cortical neurons were plated onto 8 well flaskettes that were pre-coated with laminin (10 ug/ml) or laminin with increasing concentrations of CSPG (ranging from 25 ug/ml to 250 ug/ml). Laminin is a potent neurite promoting matrix protein, but in the presence of CSPG, this activity is significantly reduced (Snow et al., 2002). Varying amounts of nanospheres and/or microspheres (containing either cABC or BSA as a control) were added two days post cell plating, and the cell morphology was documented. The nanospheres and/or microspheres were left in the cultures for two days, after which the cultures were fixed with 4% paraformaldehyde and analyzed for neurite outgrowth.

Figure 4:
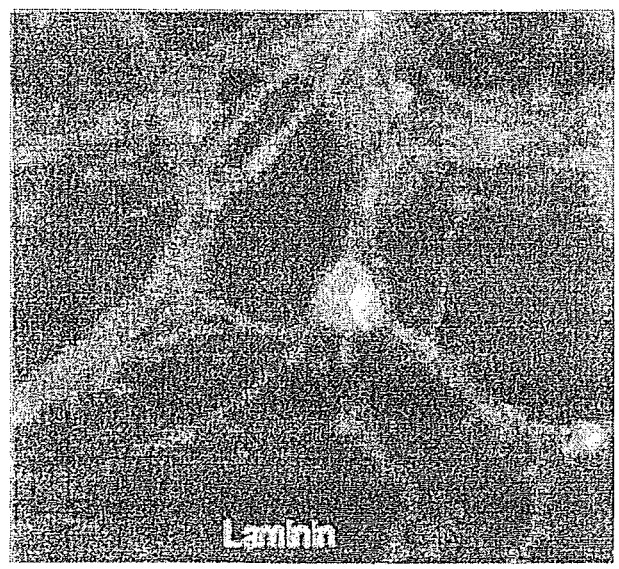
FIG. 4 shows neurite outgrowth on a am n-coated substrate.
Figure 5:
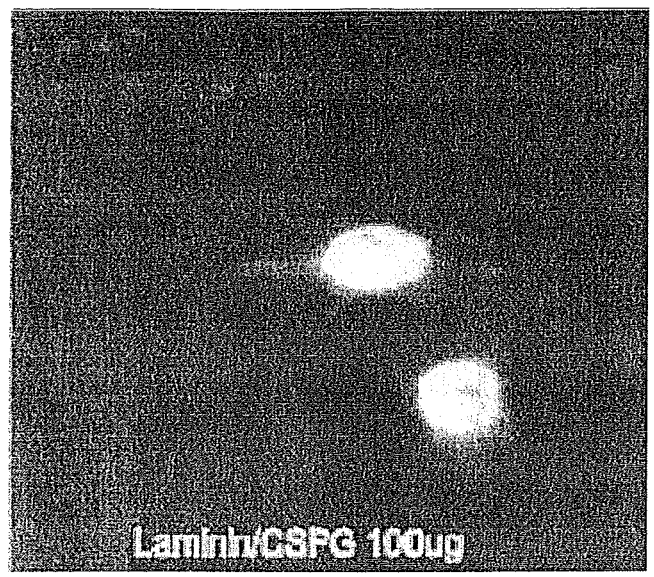
FIG. 5 shows neurite outgrowth on a substrate coated with laminin and chondroitin sulfate proteoglycans (CSPG).
Figure 6A:
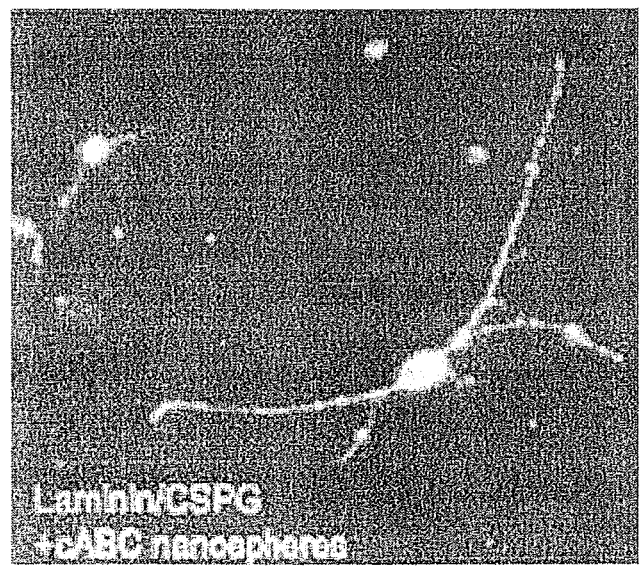
FIGS. 6A-6C show neurite outgrowth results on substrates that were coated with laminin and chondroitin sulfate proteoglycans (CSPG) and then applied with cABC-loaded nanospheres and/or microspheres.
Figure 6B:
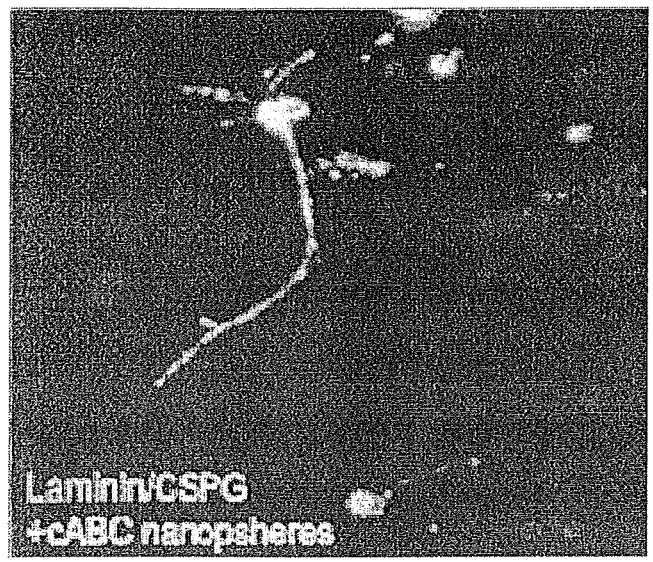
Figure 6C:

Results:

Primary neurons plated onto laminin alone extended long processes 24 hours post plating, as shown in FIG. 4; those neurons plated onto concentrations of CSPG (100 ug/ml and up) were rounded cells that rarely had processes, as shown in FIG. 5. With the addition of cABC-loaded nanospheres, the process outgrowth was enhanced, suggesting that the released cABC was digesting the CSPG, and removing proteoglycan sidechains that inhibit process outgrowth, as shown in FIGS. 6A-6C. As observed with the PC12 cells, there was no cellular toxicity observed with the addition of nanospheres loaded with either BSA or cABC.

The following table shows quantitative neurite outgrowth on the laminin/CSPG substrates where cABC-loaded nanosphere were added.

TABLE I

| Amount of cABC-Loaded Nanospheres added | Cells with Processes | Average Neurites per Cell | Average Length of Neurites (μm) |
|---|---|---|---|
| — | 1% | 0.5 ± 0.1 | 15.6 ± 1.1 |
| 5 μl | 3% | 1.1 ± 0.12 | 23.0 ± 2.4 |
| 10 μl | 20% | 1.3 ± 0.19 | 40.5 ± 3.3 |
| 20 μl | 60% | 1.5 ± 0.18 | 94.1 ± 9.7 |

The above data represents the mean and standard error for each condition. The data was obtained from analysis of 50 cells from 3 repetitions of the experiments. Addition of BSA loaded nanospheres was used as a control in these experiments, and did not enhance neurite outgrowth under any condition (data not shown).

The above experiments demonstrate that biodegradable nanospheres and/or microspheres can be prepared, which can serve as useful delivery systems for a number of substances, including chondroitinase ABC or BRDU. The release was immediate and sustained, which could work well in an injury paradigm. Most importantly, there was no toxicity observed with any of the preparations tested in cell systems, suggesting that the nanospheres and/or microspheres were safe in vitro. The next step was to test them in vivo, to examine their properties of degradation and look for any deleterious effects.

III. In Vivo Studies

In order to determine the efficacy of nanospheres and/or microspheres as a drug delivery system, a reproducible SCI model was constructed. A weight drop impactor system that damages thoracic propriospinal axons (TPS) and corticospinal tract axons was employed.

Analysis of Thoracic Propriospinal Axons After SCI

Cells were retrogradely labeled with fluorogold (5 μl injection of 3% fluorogold, FG, a dye that is incorporated at the intact or damaged ends of axons and transported retrogradely to label the cell body of the axon) by injecting FG at the T13-L1 vertebral level in non-injured adult rats (N=4), and 1 week after 12.5 mm (N=4) or 50 mm Impactor injury (N=4) at T9-T10. An additional group of 3 rats received the FG injection 4 days prior to 50 mm weight drop injury and survived for 1 week after 50 mm SCI at T9-T10. In thoracic spinal cord, cells were retrogradely labeled throughout the dorsal and intermediate gray matter in uninjured animals, but few neurons were retrogradely labeled from FG injections below a 50 or 12.5 mm Impactor injury. The total number of retrograde labeled neurons in high and midthoracic spinal cord (T1-T8) from non-injured animals was significantly higher than that seen in animals after contusion injury. Essentially, no labeled cells are found rostral to the lesion site (P=0.006). However, most TPS neurons survived axotomy, since prelabeled TPS neurons were found in similar numbers 1 week after SCI. Propriospinal axons anterogradely labeled with fluororuby form reactive endings rostral to SCI or terminate in the gray matter at this level. Propriospinal axons in the lateral funiculus at ~T8 spinal level were shown branching toward the intermediate gray matter in this horizontal section, many forming terminal boutons in the gray matter. Thus, TPS axons are consistently completely damaged by SCI and are a short-axon system available to study axonal regeneration in addition to the corticospinal tract that is also completely damaged by this type of injury. A SCI model that can be used to test the microspheres as a drug delivery system in vivo was thus established.

Nanosphere/Microsphere Injections After SCI:

A control study was first conducted in comparing the lesion site 3 weeks after 25 mm SCI in a control group (N=3) and in groups where only poly (DL-lactic-co-glycolic) acid 85/15 nanospheres/microspheres (N=3) or nanospheres/microspheres in which BSA was incorporated (N=3) were injected in the lesion epicenter 1 week after SCI (20 ul using a 26 gauge needle; nanospheres/microspheres were injected slowly by hand or using a Picospritzer). Preliminary findings of the first two operates (one injection of nanospheres/microspheres alone, one with BSA encapsulated nanospheres/microspheres) showed little post-injection behavioral effect, and no obvious inflammatory response, but a detailed analysis is being conducted.

Further, nanospheres having sizes ranging from about 250 nm to about 750 nm and loaded with cABC/BSA mixtures or pure BSA were injected to SCI lesion site in rats after 25 mm SCI. The animals were euthanized by perfusion/fixation two weeks after the 25 mm SCI with 4% paraformaldehyde.

The in vivo CSPG degradation can be measured in two ways. First, CS56 antibody can recognize intact CSPG molecules, so the in vivo CSPG degradation can be readily detected by a decrease in the CS56 reactivity. Second, 2B6 antibody can recognize part of the core protein that is exposed after the enzymatic degradation of CSPG by the cABC enzyme, so in vivo degradation of CSPG can also be detected by an increase in 2B6 reactivity.

Therefore, frozen spinal cord sections obtained from the test animals were immunostained by using the CS56 antibody and the 2B6 antibody.

Figure 7:
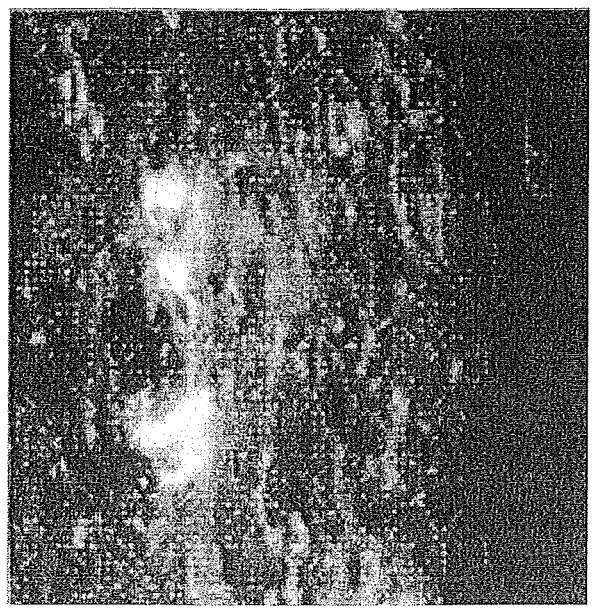
FIG. 7 shows in vivo CS56 immunoreactivity after injection of BSA-loaded nanospheres at a spinal cord injury (SCI) site.
Figure 8:
FIG. 8 shows in vivo 2B6 immunoreactivity after injection of BSA-loaded nanospheres at a spinal cord injury (SCI) site.
Figure 9:
FIG. 9 shows in vivo CS56 immunoreactivity after injection of cABC-loaded nanospheres at a spinal cord injury (SCI) site.
Figure 10:
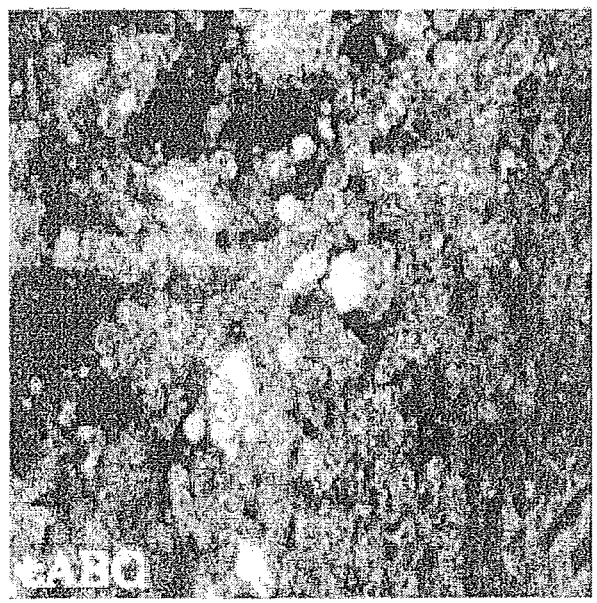
FIG. 10 shows in vivo 2B6 immunoreactivity after injection of cABC-loaded nanospheres at a spinal cord injury (SCI) site.

Results:

In vivo injection of BSA-loaded nanospheres in the SCI site had no effect on the CSPG expression, as shown by the CS56 and 2B6 assays. Specifically, FIG. 7 shows that no significant decrease in CS56 reactivity was observed after injection of the BSA-loaded nanospheres, and FIG. 8 shows no significant increase in the 2B6 reactivity was observed. In contrast, FIG. 9 shows significant decrease in CS56 reactivity after injection of the cABC-loaded nanospheres, indicating a reduction in CSPG expression, and FIG. 10 shows significant increase in the 2B6 reactivity, indicating that the cABC released from the nanospheres degraded the CSPG present at the lesion site.

Further, the nanospheres remained at the injury site, with little or no movement. More importantly, the injected nanospheres induced only a minimal inflammatory response in the cells in vivo.

Therefore, nanospheres of the present invention successfully localized cABC at the SCI site for reduction of the expression of the inhibitory CSPG molecules in vivo, without causing any adverse in vivo reactions.

Example 2

In this example, the surface properties of the nanospheres and/or microspheres were modified to specifically target CSPG. Since CSPG is a negatively charged molecule, the nanospheres and/or microspheres were positively charged. The charge attraction targeted the nanospheres and/or microspheres directly to the glial scar and CSPG deposits.

First, adhesion assays were performed, using tissue culture plastic coated with purified CSPG. Twelve well plates were coated with 1 mg/ml CSPG overnight. The dishes were rinsed with PBS five times to remove any excess CSPG. Just prior to the addition of microspheres, PBS was removed. Microspheres were weighed out and resuspended in PBS to a concentration of 10 mg/ml. A 50 µl aliquot was placed in the center of the dish and allowed to sit for 30 minutes at room temperature. The wells were washed a minimum of five times with PBS. Any microspheres remaining in the well were imaged on a Zeiss Axiophot using a 10× objective. Protein release was also measured from the charged BSA microspheres to determine the amount and duration of BSA release. Microspheres were weighed and resuspended in 1 ml of PBS; aliquots from the suspension were taken every day for 1 week, and the protein levels were measured using a Pierce BCA protein measurement kit. The results demonstrate that the cationic microspheres were highly attracted to the CSPG substrate, and generated a sustained release of protein over time. Thus, they were an excellent delivery system for targeting cABC directly to the CPSG deposits in the glial scar in vivo.

Figure 11:
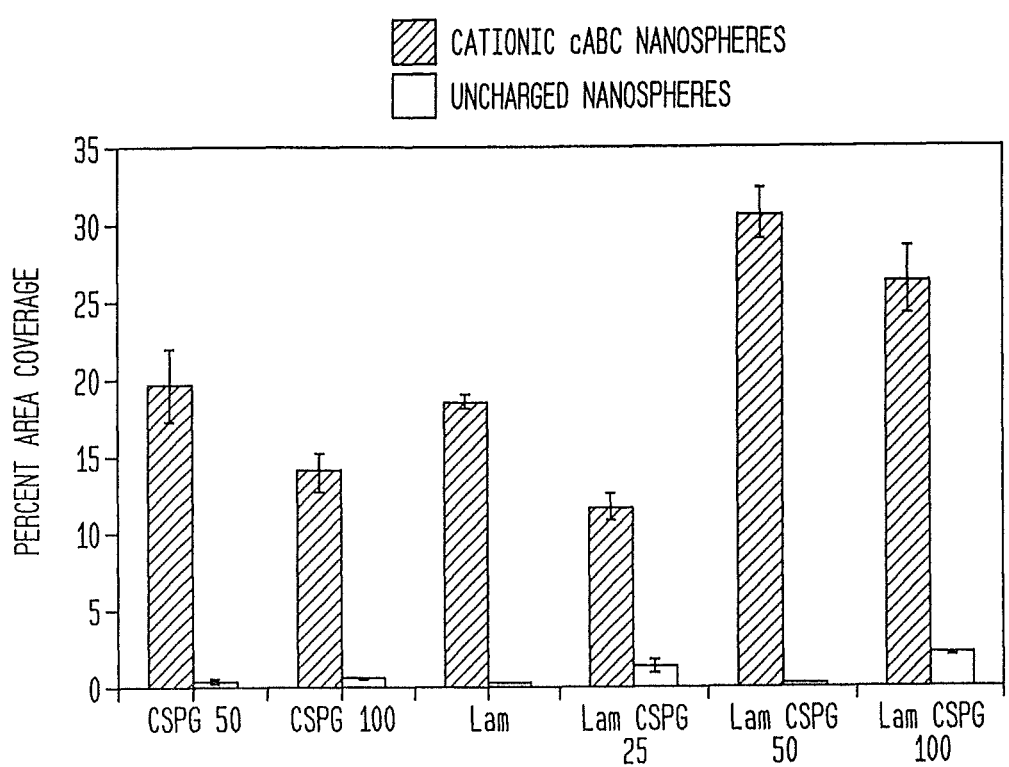
FIG. 11 shows adhesion results of uncharged and negatively charged nanospheres to substrates coated with pure CSPG or mixtures of laminin and CSPG.

Adhesion of negatively charged nanospheres to CSPG was also tested, by using tissue culture plastic coated with either purified CSPG at various concentrations (e.g., 50 µg/ml and 100 µg/ml) or laminin/CSPG mixtures with increasing concentrations of CSPG (ranging from 25 µg/ml to 100 µg/ml). Adhesion was quantified by analyzing the percentage coverage of uncharged and negatively charged nanospheres, and the results are shown in FIG. 11.

The ability of the microspheres to release cABC in vitro was tested in a neurite outgrowth assay. Primary cortical neurons from E20 neonatal rats were dissociated and plated on various substrates, including laminin (10 µg/ml) or laminin (10 µg/ml) mixed with CSPG (100 µg/ml or 250 µg/ml). Cells were in culture for 2 days prior to adding the microspheres. At the end of day two, a 10 mg/ml suspension of microspheres in PBS was prepared, and aliquots of 5 µl, 10 µl or 20 µl were added to the cultures. The cells remained in culture for two additional days, after which they were fixed in 4% paraformaldehyde and stained for neurofilament protein to label axons.

After 4 days in culture, control cultures on laminin showed robust neurite outgrowth, with a network of processes surrounding all the cell bodies. The presence of microspheres, either BSA or cABC had no effect on cell viability or process outgrowth on laminin. Neurons plated on laminin mixed with CSPG (250 µg/ml) showed little process outgrowth after 4 days in culture, while the addition of 20 µl of cABC microspheres restored significant process elongation in the cultures two days after addition.

This data demonstrates that the slow release of cABC encapsulated in microspheres was an effective method for restoring axon growth on an inhibitory substrate.

Example 3

In this study, nanospheres containing cABC in accordance with the present invention were used to effectively reduce scar formation and enhance axonal sprouting after the most common type of spinal cord injury in man, spinal contusion injury (SCI). Nanospheres were prepared from poly(lactic-co-glycolic acid) (PLGA) using an emulsification-diffusion process such as described, for example, in Quintanar-Guerrero et al., "Influence of stabilizing agents and preparative variables on the formation of poly(D,L-latic acid) nanoparticles by an emulsification-diffusion technique", Int. J. Pharm. 143:133-141 (1996) and Kwon et al., "Preparation of PLGA nanoparticles containing estrogen by emulsification-diffusion method", Coll. And Surf. A: Physicochem and Eng. Asp. 182:123-130 (2001). The surface charge on the nanospheres was modified by the stabilizer that was used; uncharged nanospheres were made using poly(vinyl alcohol) (PVA) as a stabilizer, while cationic nanospheres were prepared using didodecyl dimethyl ammonium bromide (DMAB). Coumarin-6 was incorporated as a marker in some compositions, in order to visualize the distribution of nanospheres at the lesion site after injection in vivo.

Nanospheres were characterized for their mean particle diameter and size distribution by atomic force microscopy. While the average nanosphere diameter was 307±132 nm, there was clearly a range of particle sizes generated with this manufacturing process. An analysis of nanosphere preparations showed that 91% of the population had a diameter between 100-500 nm, while 63% of the nanospheres were in the range of 250-750 nm. Nanospheres in this size range are desirable because of the ease of injection for use in SCI studies.

It was hypothesized that nanospheres with a cationic charge (stabilized with DMAB) would show greater adhesion to negatively charged CSPG-rich substrates, as compared to uncharged nanospheres (stabilized with PVA). An in vitro adhesion assay demonstrated the effect of surface charge on adhesion to CSPG. Cationic nanospheres showed significantly higher adhesion to all substrates as compared to the uncharged particles ($p<0.01$). The presence of BSA or cABC in the nanospheres did not affect the adhesion. These data demonstrate that cationic surface modification can serve as a means of targeting nanospheres to negatively charged CSPG-rich regions of the glial scar in vivo.

To assess the enzymatic activity of cABC released from nanospheres two types of assays were performed. The enzymatic activity of cABC released from nanospheres over a two week period was measured in vitro. Aliquots from a suspension of nanospheres were taken every day, and tested for the ability to digest CSPG. The digested CSPG was detected on a Western blot probed with the monoclonal antibody 2B6, which only recognizes the 4-sulfated chondroitin sulfate stub remaining after cABC digestion and intact CSPG was detected with CS-56, which recognizes the sulfated chain of native CSPG. There was a significant increase in 2B6 reactivity and a decrease in CS-56 reactivity, which demonstrated an increase in cABC activity over time. These data suggest that there was a sustained release of active cABC from the nanospheres, and that the enzymatic activity of the released enzyme appears to be long lasting. Release of the carrier molecule BSA was detected over a one month time course, which suggests that this particular formulation may release active enzyme for longer than two weeks.

If active cABC is released from the nanospheres, it would be able to digest CSPG deposits that inhibit neurite outgrowth. This was demonstrated in neurite outgrowth assays, where neurons plated on a CSPG substrate were able to extend processes in the presence of cABC nanospheres. Primary neurons plated onto laminin alone extended long processes by 24 hours post-plating; those neurons plated onto laminin and CSPG were less likely to extend neurites even after several days in culture. Even in the presence of laminin, as the concentration of CSPG increased, the number of cells bearing processes decreased, along with the length of these processes. At high concentrations of CSPG (100 µug/ml), the cells were attached, but rounded and very rarely had processes. With the addition of cABC nanospheres, process outgrowth was enhanced on a CSPG substrate, suggesting that the released cABC was digesting the CSPG and removing those GAG side-chains that inhibit process outgrowth. On the highest concentration of CSPG (100 µg/ml), there was an increase in process elongation in the presence of increasing amounts of cABC nanospheres, which is evident two days post addition. At longer times, the extent of neurite elongation approached that of the laminin control. There was no cellular toxicity observed with the addition of nanospheres, as the number of cells remained constant for the duration of the experiments. Taken together, the in vitro studies demonstrate that PLGA nanospheres can be used successfully to deliver active cABC for a minimum of two weeks.

Nanospheres were injected into rat spinal cord following a contusion injury to demonstrate their ability to deliver active cABC that will degrade CSPGs in the glial scar in vivo. The injury was a 25 mm weight drop using an NYU impactor, at the T9-T10 spinal level (SCI). Nanospheres were injected immediately after injury at two sites, one rostral and one caudal within the lesion using a microinjection apparatus.

Experimental groups included animals that received injections of cABC/BSA nanospheres (N=4) or BSA nanospheres (N=4) per time point. The deposition of CSPGs at the lesion site was examined at 5, 7, 10 and 14 days post injury by immunohistochemistry. The expression of the intact CSPG molecule was determined using the CS-56 antibody, while the 2B6 antibody was used to detect the CSPGs after cABC degradation. The two week time course was chosen as this is the time to peak expression of CSPGs at the lesion site. The appearance of 2B6 immunoreactivity at the lesion site was an indication that released cABC had degraded these CSPG deposits.

There was a significant increase in 2B6 reactivity over time in animals that received injections of cABC/BSA nanospheres, as compared to those animals that received nanospheres that release BSA alone. 2B6 staining was observed in the vicinity of cABC nanospheres; in contrast, there was very little immunoreactivity in sections from animals that received BSA nanospheres. While there was significant 2B6 staining after 5 days, the intensity increased over the 2 week time course. This can quantitated by stereology. In the presence of cABC, there was a four-fold increase in the volume of 2B6 immunostaining with cABC nanospheres, as compared to the control BSA nanospheres at 5 and 7 days post injection. This increased to a 5 fold difference between cABC and BSA nanosphere treatment at 10 and 14 days. The observed increase in 2B6 staining with time indicated that the cABC nanospheres were releasing active cABC over time in vivo, which continually degraded CSPG being produced at the lesion site. In contrast, there was little 2B6 staining in the presence of the BSA nanospheres over the time course of the experiment.

A concomitant reduction in the volume of CS-56 immunoreactivity in the lesion site over the same two week period further confirmed the findings with 2B6 immunoreactivity. The CS-56 antibody recognized intact CSPGs expressed in the glial scar, but did not react with CSPGs that have the GAG side chains removed with cABC digestion. In the presence of BSA nanospheres, there was significant CS-56 reactivity at both 5 and 14 days post injury. However, the reactivity was decreased at 5 days in the presence of cABC nanospheres, and this was further reduced at 14 days. These data suggest that the CSPGs expressed in the lesion were being digested in the presence of cABC nanospheres. The average volume of CS56 immunoreactivity was approximately 2 fold lower with the cABC nanospheres as compared to control at 5 days, and was further reduced at 14 days. An increase in CSPG digestion was indicated by the ratio of 2B6 to CS56 staining, which doubled between 5 and 14 days. It does appear that CSPG deposition has reached consistently high levels at early times post injury, given that the CS-56 reactivity over time did not increase in control conditions. Thus the increase in the ratio of 2B6:CS-56 reactivity observed with the cABC nanospheres demonstrated that the active enzyme was released over time in vivo, and cABC continued to degrade the inhibitory CSPGs present in the glial scar.

Figure 12:
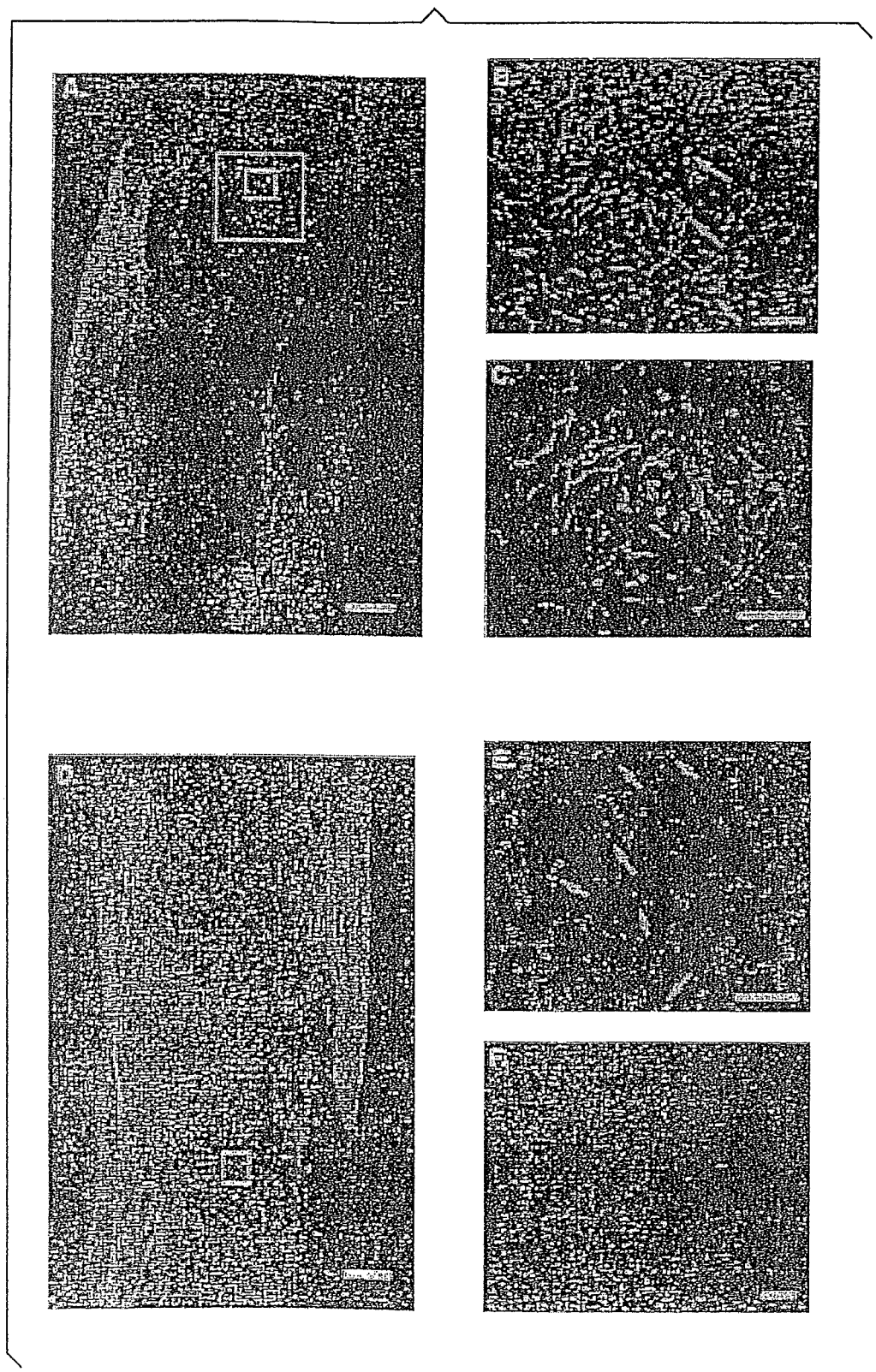
FIGS. 12A-12F are photographs showing the axonal sprouting behavior described in Example 3 of the present application.
Figure 13:
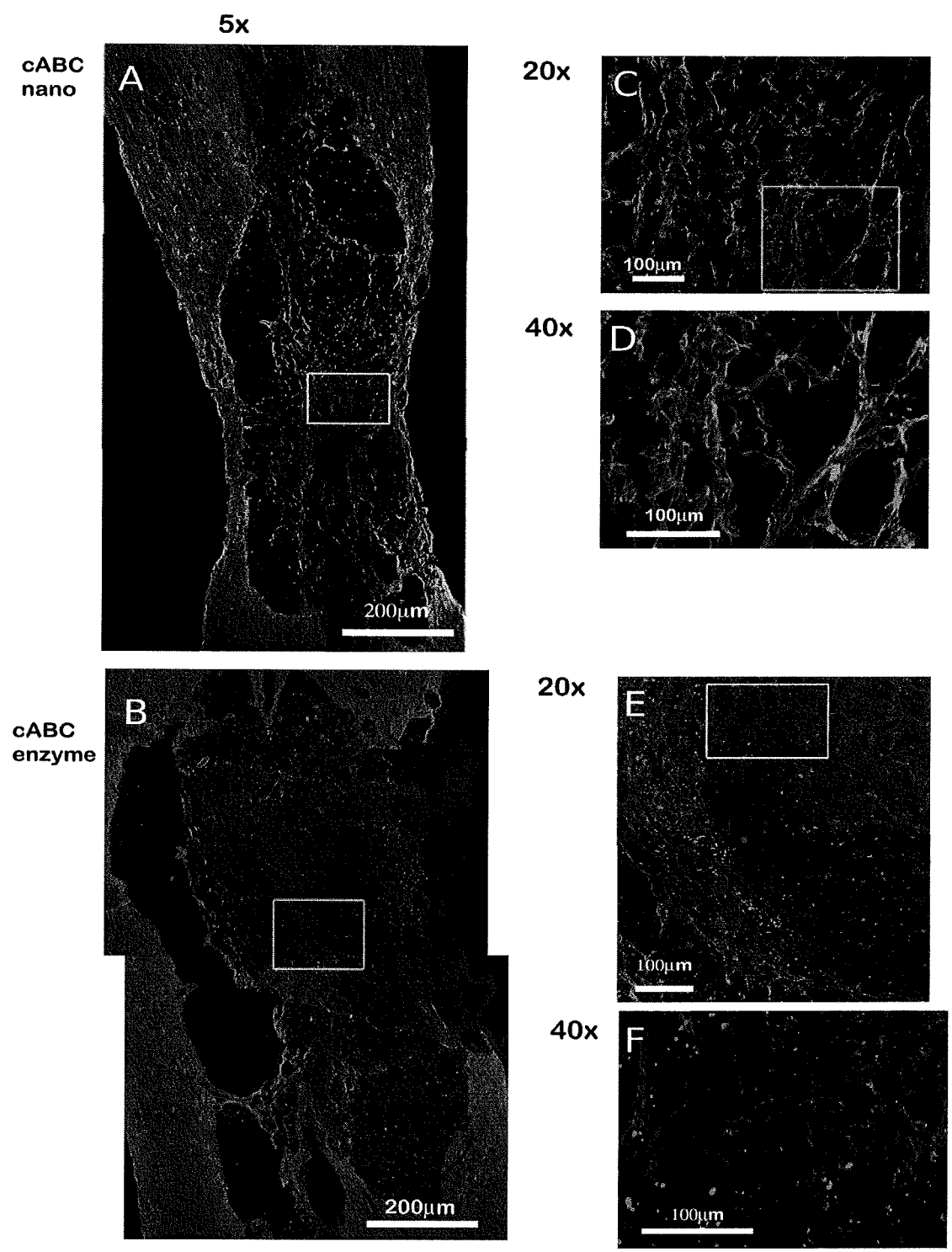
FIGS. 13A-13F are micrographs showing differences in axonal sprouting using cABC nanospheres compared to cABC injections, one month post-application.

The removal of the inhibitory GAGs at the lesion site produced an environment that enhanced process regrowth in vivo. This was evident by the numerous GAP 43 expressing processes that were oriented around nanospheres near the cABC nanosphere injection site (See, FIGS. 12A-F). At 7 and 14 days post injury, there was a significant increase in the appearance of small processes within the lesion site after cABC nanosphere injection. Since they express GAP 43, these processes likely represent new axonal sprouting at the injury site (FIGS. 12A, 12B and 12C). There was less GAP43 expression in spinal cord lesions treated with BSA nanospheres at any point during the two-week time course (FIGS. 12D and 12E), and there was no obvious orientation of the processes relative to the BSA nanospheres. This finding supports the hypothesis that cABC digestion of CSPG can convert an inhibitory environment into a permissive one, enhancing axonal regeneration.

This study demonstrated that biodegradable nanospheres successfully delivered cABC at the site of spinal cord injury, which was enzymatically active and can remove the GAG side chains that inhibit axonal regrowth. Given that new CSPG's were being continuously synthesized and deposited over the two week period immediately after SCI, the reduction in the expression of intact CSPGs with cABC indicated that the enzymatic activity was significant over time in vivo. While this study only looked at the activity of the released enzyme over the course of two weeks, both in vitro and in vivo, it is likely that the active cABC persists for much longer at the lesion, based on the sustained release of the carrier molecule BSA. This would ensure a significant reduction of the inhibitory CSPGs and provide a permissive environment for axonal regeneration after injury.

The advantages of using a nanosphere delivery system to treat SCI are clear. With one injection, the nanospheres were able to release sufficient cABC to degrade the proteoglycans in the scar, and provide a permissive environment for neurite regrowth. There was no apparent enhancement of the inflammatory response at the site of injury observed with the addition of nanospheres at any time point. There was no cellular toxicity observed with any cells in contact with nanospheres, either in vitro or in vivo. This suggests that this PLGA nanosphere formulation is compatible for injection in spinal cord. Moreover, a one time injection of a biocompatible timed release nanosphere formulation can reduce or eliminate the problems associated with infusion. In addition, the effect on axonal regeneration may be greater due to the continual localized release of cABC.

Example 4

FIGS. 13A-13F are micrographs showing differences in axonal sprouting using cABC nanospheres compared to cABC injections, one month post-application. Each set of images displays GFAP (red) to outline the lesion and GAP-43 (green) immunofluorescence to identify new axonal sprouting. The overall lesion is shown at low power (5x), while the new process outgrowth can be observed at higher magnifications (boxed areas at 20x and 40x). At four weeks post-injury, saline control animals had very little GAP-43 immunoreactivity (data not shown). Animals treated with cABC injections (B), i.e., not loaded within a carrier, showed some sprouting, although the levels seen at one month post-injury are no different than that observed at two weeks (not shown). GAP-43 levels are faint, and processes are short and very thin at both two weeks (data not shown) and one month (E, F). In contrast, treatment with cABC nanospheres allowed for extensive sprouting into and through the full length of the lesion (A). Higher magnifications reveal thick, fasciculated processes oriented longitidinally in a rostro-caudal direction (C,D). The sprouting seen at one month is much more that is observed at two weeks, demonstrating that the sustained release of cABC allows for continual process outgrowth over the one month time period.

Figure 14:
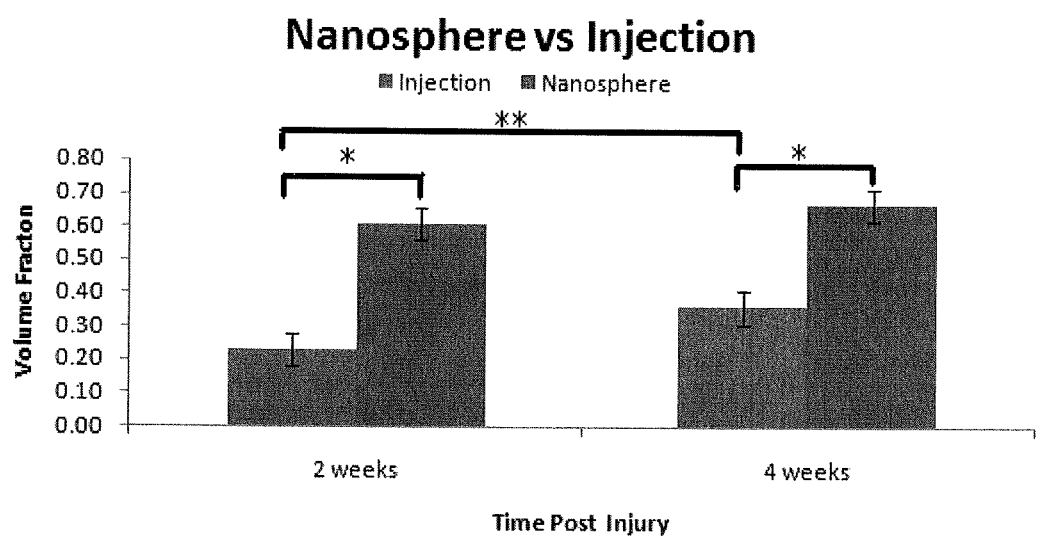
FIG. 14 is a graph showing volume fractions of digested CSPGs in the glial scar after SCI, comparing injection and nanosphere delivery of cABC.

In all cases (i.e., A and B in FIG. 13), delivery of cABC by nanospheres outperformed one time injections of cABC. FIG. 14 shows a comparison in the extent of CSPG digestion over a one month time course between a one-time cABC injection and cABC nanospheres at two weeks and one month post-injury (A). As shown, nanosphere treatment consistently yielded significantly better digestion than cABC injections ($p<0.01$). No difference was observed between two weeks and one month post-injury for cABC nanosphere-treated animals. A difference was observed between two week and one month cABC injected animals, with a slight increase in digestion over time. However, it never approaches the digestion levels obtained though use of nanospheres ($p<0.01$).

While the present invention has been particularly shown and described with respect to preferred embodiments thereof, it will be understood by those skilled in the art that the foregoing and other changes in forms and details may be made without departing from the spirit and scope of the present invention. It is therefore intended that the present invention not be limited to the exact forms and details described and illustrated, but fall within the scope of the appended claims.

What is claimed is:

1. A formulation comprising biodegradable carriers loaded with chondroitinase ABC (cABC) or a functional derivative of cABC, wherein said biodegradable carriers have a size of about 700 nm to about 15 µm, wherein the biodegradable carriers are large enough to substantially not enter cells in contact with the carriers, and wherein the biodegradable carriers release said cABC or functional derivative of cABC for up to about one year after exposure to an in vivo environment.

2. The formulation of claim 1, wherein said biodegradable carriers have a size range of about 750 nm to about 15 µm.

3. The formulation of claim 1, wherein said biodegradable carriers have a size range of about 700 nm to about 10 µm.

4. The formulation of claim 1, wherein said biodegradable carriers have a size range of about 750 nm to about 10 µm.

5. The formulation of claim 1, wherein said biodegradable carriers have a size range of about 700 nm to about 5 µm.

6. The formulation of claim 1, wherein said biodegradable carriers have a size range of about 750 nm to about 5 µm.

7. The formulation of claim 1, wherein said cABC is a recombinant cABC.

8. The formulation of claim 1, wherein said biodegradable carriers are made of a polymeric material comprising a homopolymer or a copolymer that releases said cABC or said functional derivative of cABC into a site of a spinal cord injury after an injection.

9. The formulation of claim 8, wherein said polymeric material comprises an aliphatic polyester synthesized from one or more kinds of α-hydroxycarboxylic acids, hydroxydicarboxylic acids, hydroxytricarboxylic acids, or their mixtures; poly-α-cyanoacrylic esters; amino acid polymers; or their mixtures.

10. The formulation of claim 8, wherein said polymeric material comprises an aliphatic polyester synthesized from one or more kinds of α-hydroxycarboxylic acids.

11. The formulation of claim 10, wherein said one or more kinds of α-hydroxycarboxylic acids comprise glycolic acid and lactic acid.

12. The formulation of claim 1, wherein said biodegradable carriers are comprised of polylactic acid (PLA), polyglycolic acid (PGA) or a copolymer of PLA and PGA.

13. The formulation of claim 1, wherein an outer surface of said biodegradable carriers has been modified to include a positive charge.

14. The formulation of claim 1, further comprising one or more carrier proteins selected from the group consisting of bovine serum albumin, keyhole limpet hemocyanin, ovalbumin, fetal bovine serum, thyroglobulin, and human serum albumin.

15. The formulation of claim 1, further comprising other therapeutic substances for promoting healing, reducing scar formation, or enhancing nerve repair of an spinal cord injury, wherein said other therapeutic substances are loaded in said biodegradable carriers and are selected from the group consisting of enzymes, proteins, antibodies, neurotrophins, and growth factor hormones.

16. The formulation of claim 15, wherein said other therapeutic substances are selected from the group consisting of Nerve Growth Factor (NGF), Brain-Derived Neurotrophic Factor (BDNF), Neurotrophin (NT) 3, 4/5, and 6, Ciliary Neurotrophic Factor (CNTF), Glial Cell Line-Derived Growth Factor (GDNF), Leukemia Inhibitory Factor (LIF), Interleukin 6 (IL6), Interleukin 11 (IL11), Cardiotrophin 1, Interferon α (IFNα), Interferon β (IFNβ), Tumor Necrosis Factor (TNF), decorin, antibodies blocking inhibitory proteoglycans, antibodies to myelin proteins, and antibodies to receptors of myelin proteins.

17. The formulation of claim 1, wherein said biodegradable carriers are small enough to be injectable.

18. The formulation of claim 1, wherein said biodegradable carriers remain extracellular in vitro and in vivo.

19. The formulation of claim 1, wherein said biodegradable carriers remain extracellular for about one year after injection.

* * * * *